US006699715B1

(12) United States Patent
Ledbetter et al.

(10) Patent No.: US 6,699,715 B1
(45) Date of Patent: *Mar. 2, 2004

(54) MODIFIED SFV MOLECULES WHICH MEDIATE ADHESION BETWEEN CELLS AND USES THEREOF

(75) Inventors: Jeffrey A. Ledbetter, Seattle, WA (US); Martha Hayden, Everett, WA (US); Perry Fell, Redmond, WA (US); Robert Mittler, Woodinville, WA (US); Gosta Winberg, Bromma (SE)

(73) Assignee: Bristol-Myers Squibb Co., Princeton, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/756,416

(22) Filed: Nov. 27, 1996

Related U.S. Application Data

(60) Provisional application No. 60/007,755, filed on Nov. 30, 1995.

(51) Int. Cl.$^7$ ...................... A61K 39/395; C07K 16/46; C12N 5/10

(52) U.S. Cl. ................. 435/328; 424/134.1; 424/135.1; 435/69.7; 530/387.3

(58) Field of Search ................................ 530/300, 350, 530/395, 387.3; 424/185.1, 134.1, 135.1; 435/69.3, 69.7, 328

(56) References Cited

U.S. PATENT DOCUMENTS

| | | | | |
|---|---|---|---|---|
| 5,225,538 A | | 7/1993 | Capon et al. | 530/387.3 |
| 5,359,046 A | | 10/1994 | Capon et al. | 536/23.4 |
| 5,712,149 A | * | 1/1998 | Roberts | 435/69.7 |

FOREIGN PATENT DOCUMENTS

| | | |
|---|---|---|
| WO | WO 93 19163 A | 9/1993 |
| WO | WO 96 23814 | 8/1996 |

OTHER PUBLICATIONS

Isacke et al, the Adhesion Molecule Facts Book, Second Edition, Academic Press, pp. 103 and 111, 2000.*
Janeway, Jr et al, Immunobiology: The Immune System in Health and Disease, Garland Publishing Inc, pp. A1–A10, 1997.*
Lund et al. (1991) J. Immun. 147(8):2657–2662.
Linsley et al. (1991) J. Exp. Med. 173.
Biocca and A. Cattaneo (1995) Trends in Cell Biology 5:248–252.
C.R. Newton, et al. (1994) Protein Expression and Purification 5(5):449–57.
G.F. Tu, et al. (1995) J. of Biol. Chem. 270(16):9322–6.
Hansen et al. (1980) Immunogenetics 10:247–260.
Parham, et al. (1983) J. Immunol. 131:2895–2902.
A. Barclay et al. (1993) Academic Press pp101–269.
Hayden et al. (1996) Tissue Antigen vol. 4.
Waterhouse et al. (1995) Science 270(5238):890, 985–989.
Walunas et al. (1994) Immunity 1:405–413.
Jenkins et al. (1991) J. Immunol. 147(8):2461–2466.
Gimmi et al. (1991) Proc. Natl. Acad. Sci. USA 88:6575–6579.
Azuma et al. (1992) J. Immunol. 149(4):1115–1123.
Azuma et al. (1992) J. Exp. Med. 175:353–360.
Chen et al. (1992) Cell 71:1093–1102.
Chen et al. (1992) J. Immunol. 148(8):2617–2621.
Rosenberg et al. (1986) Science 433:1318–1321.
Abbass et al. Cellular and Molecular Immunology, 2nd Edition, 1994, Chapter 7 pp. 163–164.
Gilliland et al. (1996) "Rapid and reliable cloning of antibody variable regions and generation of recombinant single chain antibody fragments," *Tissue Antigens*, 47:1–20.

* cited by examiner

*Primary Examiner*—David Saunders
(74) *Attorney, Agent, or Firm*—Keith R. Lange; Christopher A. Klein

(57) ABSTRACT

The modified sFv molecules of the present invention stimulate adhesion between cells thereby enhancing the immune response against disease. These molecules generally comprise an antigen binding site of an antibody and at least a portion of a transmembrane domain of a cell surface receptor.

7 Claims, 26 Drawing Sheets

Plasmid name: PLNC-2e12hIgG1hB7-1Tm
Plasmid size: 8290 bp

Comments/References: L6 Leader preceded by 5'-CCACC-3'; BclI in 2e12 changed to BglII; BamHI-BstBII sequence is: 5'-GGATCCTTCGAA-3'. hIgG1(Fc-mut) is from P. Linsley.

Plasmid name: PLNC-2e12hIgG1CD58GPI
Plasmid size: 8254 bp

Comments/References: CD58GPI-anchor and C-terminal signal sequence is a.a. 207–237 [base 631–739 (incl.)] of cDNA in: Seed, B. 1987. Nature, 329:840–842. XhoI-ClaI sequence is 5'-CTCGAGCATCGAT-3'

Plasmid name: PLNC-hB7-1
Plasmid size: 7498 bp

Comments/References: Human B7-1 (CD80) ATG codon is preceded by 5'-CCACC-3'.

FIG. 10A
NUCLEIC ACID SEQUENCE OF THE 2E12 sFv INCLUDING THE FC LINKER AND B7-1 TRANSMEMBRANE DOMAIN

ATT GTG CTC ACC CAA TCT CCA GCT TCT TTG GCT GTG TCT CTA GGT CAG AGA
CCC ACC ATC TCC TGC AGA GCC AGT GAA AGT GTT GAA TAT TAT GTC ACA AGT
TTA ATG CAG TGG TAC CAA CAG AAA CCCA GGA CAG CCA CCC AAA CTC CTC
ATC TCT GCT GCA TCC AAC GTA GAA TCT GGG GTC CCT GCC AGG TTT AGT GGC
AGT GGG TCT GGG ACA GAC TTC AGC CTC AAC ATC CAT CCT GTG GAG GAG GAT
GAT ATT GCA ATG TAT TTC TGT CAG CAA AGT AGG AAG GTT CTT TGG ACG TTC
GGT GGA GGC ACC AAG CTG GAA ATC AAA CGG GGT GGC GGT GGC TCG GGC GGT
GGT GGG TCG GGT GGC GGC GGA TCT CAG GTG CAG CTG AAG GAG TCA GGA CCT
GGC CTG GTG GCG CCC TCA CAG AGC CTG TCC ATC ACA TGC ACC GTC TCA GGG
TTC TCA TTA ACC GGC TAT GGT GTA AAC TGG GTT CGC CAG CCT CCA GGA AAG
GGT CTG GAG TGG CTG GGA ATG ATA TGG GGT GAT GGA AGC ACA GAC TAT AAT
TCA GCT CTC AAA TCC AGA CTG AGC ATC ACC AAG GAC AAC TCC AAG AGC CAA
GTT TTC TTA AAA ATG AAC AGT CTG CAA ACT GAT GAC ACA GCC AGA TAC TAC
TGT GCC AGA GAT GGT TAT AGT AAC TTT CAT TAC TAT GTT ATG GAC TAC TGG
GGT CAA GGA ACC TCA GTC ACC GTC TCC TCT <u>GAT</u> CCG GAG CCC AAA TCT TGT
GAC AAA ACT CAC ACA TGC CCA CCG TGC CCA GCA CCT GAA TTC GAG GGT GCA
CCG TCA GTC TTC CTC TTC CCC CCA AAA CCC AAG GAC AAC CTC ATG ATC TCC
CGG ACC CCT GAG GTC ACA TGC GTG GTG GTG GAC GTG AGC CAC GAA GAC CCT
GAG GTC AAG TTC AAC TGG TAC GTG GAC GCC GTG GAG GTG CAT AAT GCC AAG
ACA AAG CCG CGG GAG GAG CAG TAC AAC AGC ACG TAC CGG GTG GTC AGC GTC
CTC ACC GTC CTG CAC CAG GAC TGG CTG AAT GGC AAG GAG TAC AAG TGC AAG
GTC TCC AAC AAA GCC CTC CCA GCC CCC ATC GAG AAA ACC ATC TCC AAA GCC
AAA GGG CAG CCC CGA GAA CCA CAG GTG TAC ACC CTG CCC CCA TCC CGG GAT
GAG CTG AAC AAG AAC CAG GTC AGC CTG ACC TGC CTG GTC AAA GGC TTC TAT

FIG. 10B

```
CCC AGC GAC ATC GCC GTG GAG TGG GAG AGC AAT GGG CAG CCG GAG AAC AAC
TAC AAG ACC ACG CCT CCC GTG CTG GAC TCC GAC GGC TCC TTC TTC CTC TAC
AGC AAG CTC ACC GTG GAC AAG AGC AGG TGG CAG CAG GGG AAC GTC TTC TCA
TGC TCC GTG ATG CAT GAG GCT CTG CAC AAC CAC TAC ACG CAG AAG AGC CTC
TCC CTG TCT CCG GGT AAA AAC CTG CTC CCA TCC TGG GCC ATT ACC TTA ATC
TCA GTA AAT GGA ATT TTT GTC ATA TGC TGC CTG ACC TAC TGG TTT GCC CCA
```

FIG. IIA

NUCLEIC ACID SEQUENCE OF THE 2E12 sFv INCLUDING THE FC LINKER AND GPI TRANSMEMBRANE DOMAIN

ATT GTG CTC ACC CAA TCT CCA GCT TCT TTG GCT GTG TCT CTA GGT CAG AGA

CCC ACC ATC TCC TGC AGA GCC AGT GAA AGT GTT GAA TAT TAT GTC ACA AGT

TTA ATG CAG TGG TAC CAA CAG AAA CCCA GGA CAG CCA CCC AAA CTC CTC

ATC TCT GCT GCA TCC AAC GTA GAA TCT GGG GTC CCT GCC AGG TTT AGT GGC

AGT GGG TCT GGG ACA GAC TTC AGC CTC AAC ATC CAT CCT GTG GAG GAG GAT

GAT ATT GCA ATG TAT TTC TGT CAG CAA AGT AGG AAG GTT CTT TGG ACG TTC

GGT GGA GGC ACC AAG CTG GAA ATC AAA CGG GGT GGC GGT GGC TCG GGC GGT

GGT GGG TCG GGT GGC GGC GGA TCT CAG GTG CAG CTG AAG GAG TCA GGA CCT

GGC CTG GTG GCG CCC TCA CAG AGC CTG TCC ATC ACA TGC ACC GTC TCA GGG

TTC TCA TTA ACC GGC TAT GGT GTA AAC TGG GTT CGC CAG CCT CCA GGA AAG

GGT CTG GAG TGG CTG GGA ATG ATA TGG GGT GAT GGA AGC ACA GAC TAT AAT

TCA GCT CTC AAA TCC AGA CTG AGC ATC ACC AAG GAC AAC TCC AAG AGC CAA

GTT TTC TTA AAA ATG AAC AGT CTG CAA ACT GAT GAC ACA GCC AGA TAC TAC

TGT GCC AGA GAT GGT TAT AGT AAC TTT CAT TAC TAT GTT ATG GAC TAC TGG

GGT CAA GGA ACC TCA GTC ACC GTC TCT TCT GAT CCG GAG CCC AAA TCT TGT

GAC AAA ACT CAC ACA TGC CCA CCG TGC CCA GCA CCT GAA TTC GAG GGT GCA

CCG TCA GTC TTC CTC TTC CCC CCA AAA CCC AAG GAC AAC CTC ATG ATC TCC

CGG ACC CCT GAG GTC ACA TGC GTG GTG GTG GAC GTG AGC CAC GAA GAC CCT

GAG GTC AAG TTC AAC TGG TAC GTG GAC GCC GTG GAG GTG CAT AAT GCC AAG

ACA AAG CCG CGG GAG GAG CAG TAC AAC AGC ACG TAC CGG GTG GTC AGC GTC

CTC ACC GTC CTG CAC CAG GAC TGG CTG AAT GGC AAG GAG TAC AAG TGC AAG

GTC TCC AAC AAA GCC CTC CCA GCC CCC ATC GAG AAA ACC ATC TCC AAA GCC

AAA GGG CAG CCC CGA GAA CCA CAG GTG TAC ACC CTG CCC CCA TCC CGG GAT

GAG CTG ACC AAG AAC CAG GTC AGC CTG ACC TGC CTG GTC AAA GGC TTC TAT

FIG. 11B

CCC AGC GAC ATC GCC GTG GAG TGG GAG AGC AAT GGG CAG CCG GAG AAC AAC

TAC AAG ACC ACG CCT CCC GTG CTG GAC TCC GAC GGC TCC TTC TTC CTC TAC

AGC AAG CTC ACC GTG GAC AAG AGC AGG TGG CAG CAG GGG AAC GTC TTC TCA

TGC TCC GTG ATG CAT GAG GCT CTG CAC AAC CAC TAC ACG CAG AAG AGC CTC

TCC CTG TCT CCG GGT AAA <u>TAT</u> GCA CTT ATA CCC ATA CCA TTA GCA GTA ATT

ACA ACA TGT ATT GTG CTG TAT ATG AAT GTT CTT

FIG.12A

```
  1  GTCGACATTG  TGCTCACCCA  ATCTCCAGCT  TCTTTGGCTG  TGTCTCTAGG
 51  TCAGAGAGCC  ACCATCTCCT  GCAGAGCCAG  TGAAAGTGTT  GAATATTATG
101  TCACAAGTTT  AATGCAGTGG  TACCAACAGA  AACCAGGACA  GCCACCCAAA
151  CTCCTCATCT  CTGCTGCATC  CAACGTAGAA  TCTGGGGTCC  CTGCCAGGTT
201  TAGTGGCAGT  GGGTCTGGGA  CAGACTTCAG  CCTCAACATC  CATCCTGTGG
251  AGGAGGATGA  TATTGCAATG  TATTTCTGTC  AGCAAAGTAG  GAAGGTTCCT
301  TGGACGTTCG  GTGGAGGCAC  CAAGCTGGAA  ATCAAACGGG  GTGGCGGTGG
351  CTCGGCGGT   GGTGGGTCGG  GTGGCGGCGG  ATCTCAGGTG  CAGCTGAAGG
401  AGTCAGGACC  TGGCCTGGTG  GCGCCCTCAC  AGAGCCTGTC  CATCACATGC
451  ACCGTCTCAG  GGTTCTCATT  AACCGGCTAT  GGTGTAAACT  GGGTTCGCCA
501  GCCTCCAGGA  AAGGGTCTGG  AGTGGCTGGG  AATGATATGG  GGTGATGGAA
551  GCACAGACTA  TAATTCAGCT  CTCAAATCCA  GACTGAGCAT  CACCAAGGAC
601  AACTCCAAGA  GCCAAGTTTT  CTTAAAAATG  AACAGTCTGC  AAACTGATGA
651  CACAGCCAGA  TACTACTGTG  CCAGAGATGG  TTATAGTAAC  TTTCATTACT
701  ATGTTATGGA  CTACTGGGGT  CAAGGAACCT  CAGTCACCGT  CTCCTCTGAT
751  CA
```

FIG. 12B

```
(Linear)  (Six Base) Map of:  Rgamma.   check:  7812 from: 1 to: 767
LOCUS    HUIGG1 MUT    767 BP DS-DNA
DEFINITION
ACCESSION
KEYWORDS
SOURCE
BASE COUNT      185 A        253 C       207 G       122 T       0 OTHER with 139 enzymes: *
                  B                              B
                  s                              s
                  p                              p
       BB  BB    B1                              1    A      E
       as  ss    a2                    N         2    1      Ac
       mt  ap    n8                    s         8    w      po
       HY  WE    I6                    P         6    N      oR
       II  II    II                    I         I    I      II
       GGATCCGGAGCCCAAATCTTGTGACAAAACTCACACATGCCCACCGTGCCCAGCACCTGA
     1 ------------------------------------------------------------ 60 b      D  P  E  P  K  S  C  D  K  T  H  T  C  P  P  C  P  A  P  E

B
                       s
              A        p
              1       1H                                      B
              W       B2g              E        S             Ms
              4       b8i              a        t             sp
              4       s6A              r        y             1H
              I       III              I        I             II
       ATTCGAGGGTGCACCGTCAGTCTTCCTCTTCCCCCCAAAACCCAAGGACACCCTCATGAT
    61 ------------------------------------------------------------ 120 b      F  E  G  A  P  S  V  F  L  F  P  P  K  P  K  D  T  L  M  I

B                                               B
              s                                               s
              u              MN                               BuD
              3              ss                               b3r
              6              1p                               s6d
              I              II                               III
       CTCCCGGACCCCTGAGGTCACATGCGTGGTGGTGGACGTGAGCCACGAAGACCCTGAGGT
   121 ------------------------------------------------------------ 180 b      S  R  T .P  E  V  T  C  V  V  V  D  V  S  H  E  D  P  E  V

N
                       B                                      sS
                       s                                      D pa
                       a                                      s Bc
                       A                                      a II
                       I                                      I II
       CAAGTTCAACTGGTACGTGGACGCCCTCCAGGTCCATAATGCCAAGACAAAGCCGCGGGA
   181 ------------------------------------------------------------ 240
```

FIG.12C

```
b    K  F  N  W  Y  V  D  G  V  E  V  H  N  A  K  T  K  P  R  E  -
     B                 B                       B              E
     s                 s              B        s              c
     e                 a              s        g              o
     R                 A              I                       N
     I                 I                                      I
     GGAGCAGTACAACAGCACGTACCGGGTGGTCAGCGTCCTCACCGTCCTGCACCAGGACTG
 241------------------------------------------------------------300 b    E  Q  Y  N  S  T  Y  R  V  V  S  V  L  T  V  L  H  Q  D  W  -
                                      B                       M
                                      s                       m
                                      a                       e
                                      I                       I
     GCTGAATGGCAAGGAGTACAAGTGCAAGGTCTCCAACAAAGCCCTCCCAGCCCCCATCGA
 301------------------------------------------------------------360 b    L  N  G  K  E  Y  K  C  K  V  S  N  K  A  L  P  A  P  I  E  -
                                                    B
                                                    s
                                                    P
                                            D       1
                                   A        r       4
                                   v        d       0
                                   a        I       7
                                   I                I
     GAAAACCATCTCCAAAGCCAAAGGGCAGCCCCGAGAACCACAGGTGTACACCCTGCCCCC
 361------------------------------------------------------------420 b    K  T  I  S  K  A  K  G  Q  P  R  E  P  Q  V  Y  T  L  P  P  -
                              DS                       B
        A  S                  re                       s
        v  m                  dx                       p
        a  a                  IA                       M
        I  I                  II                       I
     ATCCCGGGATGAGCTGACCAAGAACCAGGTCAGCCTGACCTGCCTGGTCAAAGGCTTCTA
 421------------------------------------------------------------480 b    S  R  D  E  L  T  K  N  Q  V  S  L  T  C  L  V  K  G  F  Y  -
                                                B
              MD                                s
              SB                                r
              1a                                D
              II                                I
     TCCCAGCGACATCGCCGTGGAGTGGGAGAGCAATGGGCAGCCGGAGAACAACTACAAGAC
 481------------------------------------------------------------540 b    P  S  D  I  A  V  E  W  E  S  N  G  Q  P  E  N  N  Y  K  T  -
        B                                                       B
        s                                  S     M        D     s
        p                                  f     m        s     p
        G                                  C     e        a     M
        I                                  I     I        I     I
     CACGCCTCCCGTGCTGGACTCCGACGGCTCCTTCTTCCTCTACAGCAAGCTCACCGTGGA
```

B    T  P  P  V  L  D  S  D  G  S  F  F  L  Y  S  K  L  T  V  D  -
                           B        X              B     N
                           b        m              s     s
                           s        n              g     I
                           I        I              I     I
     CAAGAGCAGGTGGCAGCAGGGGAACGTCTTCTCATGCTCCGTGATGCATGAGGCTCTGCA
     601 ----------------------------------------------------------- 660 b    K  S  R  W  Q  Q  G  N  V  F  S  C  S  V  M  H  E  A  L  H  -
                                                    BBG
             ES                                     EEssdN
             aa                                     aariia
             rp                                     egeeie
             II                                     IIIIII CAACCACTACACGCAGAAGAGCCTCTCCCTGTCTCCGGGTAAATGAGTGCGACGGCCGGC
     661 ----------------------------------------------------------- 720 b    N  H  Y  T  Q  K  S  L  S  L  S  P  G  K  *  V  R  R  P  A  -
                                 B
                                 s
                                 p
                    B            B1           B
                    s   A   S    a2    s  B   M     X
                    r   v   m    n8    I  s   s     b
                    B   a   a    I6    E  I   I     a
                    I   I   I    II    I  I   I     I

AAGCCCCGCTCCCCGGGCTCTCGCGGTCGCACGAGGATGCTTCTAGA
     721 ----------------------------- 767 b    S  P  A  P  R  A  L  A  V  A  R  G  C  F  *  -
```

Enzymes that do cut:

| | | | | | | | |
|---|---|---|---|---|---|---|---|
| Alw44I | AlwNI | ApoI | AvaI | BamHI | BanII | BbsI | BsaI |
| BsaAI | BsaWI | BseRI | BsgI | BsiI | BsiEI | Bsp1286I | Bsp1407I |
| BspEI | BspGI | BspHI | BspMI | BsrBI | BsrDI | BsrFI | BstYI |
| Bsu36I | DrdI | DrdII | DsaI | EaeI | EagI | EarI | EcoNI |
| EcoRI | GdiII | HgiAI | MmeI | MslI | NaeI | NsiI | NspI |
| NspBII | SacII | SapI | SexAI | SfcI | SmaI | StyI | XbaI |
| XmnI | | | | | | | |

FIG. 12E

Enzymes that do not cut:

| | | | | | | | |
|---|---|---|---|---|---|---|---|
| AatII | AccI | AflII | AflIII | AgeI | ApaI | ApaBI | AscI |
| AseI | AvrII | BaeI | BanI | Bce83I | BcgI | BcgI | BclI |
| BglI | BglII | BpmI | BPUI0I | Bpu1102I | BsaBI | BsaHI | BsmI |
| BssHII | Bst1107I | BstEII | BstXI | ClaI | DraI | DraIII | Eam1105I |
| EciI | Eco47III | Eco57I | EcoO109I | EcoRV | Esp3T | FseI | FspI |
| HaeI | HaeII | HgiEII | HincII | HindIII | PhaI | KpnI | MluI |
| MscI | MunI | NarI | NcoI | NdeI | NheI | NotI | NruI |
| NspV | PacI | Pf12308I | PflMI | PmeI | PmlI | PpuMI | PshAI |
| Pspl406I | PstI | PvuI | PvuII | RleAI | RsrII | SalI | ScaI |
| SfiI | SgrAI | SnaBI | SpeI | SphI | SrfI | Sse8387I | SspI |
| SstI | StuI | SunI | SwaI | TaqII | TaqII | Tth111I | Tth111II |
| XcmI | XhoI | | | | | | |

FIG. 12F

B7-1 TRANSMEMBRANE DOMAIN

AAC CTG CTC CCA TCC TGG GCC ATT ACC TTA ATC TCA GTA AAT
GGA ATT TTT GTC ATA TGC TGC CTG ACC TAC TGG TTT GCC CCA

FIG. 12G

```
  1 GCCCGACGAGCCATGGTTGCTGGCAGCGACGCGGGGCGGGCCCTGGGGGTCCTCAGCGTGGTCTGC
  1                MetValAlaGlySerAspAlaGlyArgAlaLeuGlyValLeuSerValValCys

67 CTGCTGCACTGCTTTGGTTTCATCAGCTGTTTTTCCCAACAAATATATGGTGTTGTGTATGGGAAT
 19 LeuLeuHisCysPheGlyPheIleSerCysPheSerGlnGlnIleTyrGlyValValTyrGlyAsn
                                                                   ---

133 GTAACTTTCCATGTACCAAGCAATGTGCCTTTAAAAGAGGTCCTATGGAAAAAACAAAAGGATAAA
 41 ValThrPheHisValProSerAsyValProLeuLysGluValLeuTrpLysLysGlnLysAspLys
    CHO---

199 GTTGCAGAACTGGAAAATTCTGAATTCACAGCTTTCTCATCTTTTAAAAATAGGGTTTATTTAGAC
 63 ValAlaGluLeuGluAsnSerGluPheArgAlaPheSerSerPheLysAsnArgValTyrLeuAsp

266 ACTGTGTCAGGTAGCCTCACTATCTACAACTTAACATCATCAGATGAAGATGAGTATGAAATGGAA
 85 ThrValSerGlySerLeuThrIleTyrAsnLeuThrSerSerAspGluAspGluTyrGluMetGlu
                              ---CHO---

331 TCGCCAAATATTACTGATACCATGAAGTTCTTTCTTTATGTGCTTGAGTCTCTTCCATCTCCCACA
107 SerProAsnIleThrAspThrMetLysPhePheLeuTyrValLeuGluSerLeuProSerProThr
             ---CHO---

397 CTAACTTGTGCATTGACTAATGGAAGCATTGAAGTCCAATGCATGATACCAGAGCATTACAACAGC
129 LeuThrCysAlaLeuThrAsnGlySerIleGluValGlnCysMetIleProGluHisTyrAsnSer
                       ---CHO---

463 CATCGAGGACTTATAATGTACTCATGGGATTGTCCTATGGAGCAATGTAAACGTAACTCAACCAGT
151 HisArgGlyLeuIleMetTyrSerTrpAspCysProMetGluGlnCysLysArgAsnSerThrSer

529 ATATATTTTAAGATGGAAAATCATCTTCCACAAAAAATACAGTGTACTCTTAGCAATCCATTATTT
173 IleTyrPheLysMetGluAsnAspLeuProGlnLysIleGlnCysThrLeuSerAsnProLeuPhe

595 AATACAACATCATCAATCATTTTGACAACCTGTATCCCAAGCAGCGGTCATTCAAGACACAGATAT
195 AsnThrThrSerSerIleIleLeuThrThrCysIleProSerSerGlyHisSerArgHisArgTyr
                                                                 ---CHO---

661 GCACTTATACCCATACCATTAGCAGTAATTACAACATGTATTGTGCTGTATATGAATGTTCTTTAA
217 AlaLeuIleProIleProLeuAlaValIleThrThrCysIleValLeuTyrMetAsnValLeuEnd

727 TTGAGAAGACAATTTCTTCATTTTTAGGTATTCTGAAATGTGACAGAAAACCAGACACAACCAACT

793 CCAATTGATTGGTAACAGAAGATGAACACAACAGCATAACTAAATTATTTTAAAAACTAAAAAGCC

859 ATCTGATTTCTCATTT
```

The sites of potential N-linked glycosylation are denoted by the symbol -CHO-; the hydrophobic carboxyl terminus is underscored.

FIG. 13

9.3 sFv NUCLEOTIDE AND DEDUCED AMINO ACID SEQUENCE

```
                              LEADER
HindIII  M  E  S  D  T  L  L  L  W  V  L  L  L  W  V  P  G  S
AAGCTTATGGAGTCAGACACACTCCTGCTATGGGTGCTGCTGCTCTGGGTTCCAGGCTCC V₁L →                          10
        T  G  D  I  V  L  T  Q  S  P  A  S  L  A  V  S  L  G  Q  R
        ACTGGTGACATTGTGCTCACCCAATCTCCAGCTTCTTTGGCTGTGTCTCTAGGGCAGAGA 20            CDR1  27 a  b  c  d           30
        A  T  I  S  C  R  A  S  E  S  V  E  Y  Y  V  T  S  L  M  Q
        GCCACCATCTCCTGCAGAGCCAGTGAGAGTGTTGAATATTATGTCACAAGTTTAATGCAG 40                        50   CDR2
        W  Y  Q  Q  K  P  G  Q  P  P  K  L  L  I  F  A  A  S  N  V
        TGGTACCAGCAGAAGCCAGGACAGCCACCCAAA CTCCTCATCTTTGCTGCATCCAACGTA 60                           70
        E  S  G  V  P  A  R  F  S  G  S  G  S  G  T  N  F  S  L  N
        GAATCTGGGGTCCCTGCCAGGTTTAGTGGCAGTGGGTCTGGGACAAACTTCAGCCTCAAC 80                          90    CDR3
        I  H  P  V  D  E  D  D  V  A  M  Y  F  C  Q  Q  S  R  K  V
        ATCCATCCTGTGGACGAGGATGATGTTGCAATGTATTTCTGTCAGCAAAGTAGGAAGGTT 100                                 (GLY₄SER)₃
        P  Y  T  F  G  G  G  T  K  L  E  I  K  R  A  S  G  G  G  G
        CCTTACACGTTCGGAGGGGGGACCAAGCTGGAAATAAAACGGGCTTCG GGTGGTGGCGGT
                                                "Jĸ1"
                                                              V_H →
                                                               1
        S  G  G  G  G  S  G  G  G  G  S  L  A  Q  V  Q  L  K  E  S
        TCTGGAGGTGGCGGTTCAGGCGGCGGTGGATCCCTGGCTCAGGTGCAGCTGAAGGAGTCA
                                       BamHI
                      10                         20
        G  P  G  L  V  T  P  S  Q  S  L  S  I  T  C  T  V  S  G  F
        GGACCTGGCCTGGTGACGCCCTCACAGAGCCTGTCCATCACTTGTACTGTCTCTGGGTTT 30     CDR1                    40
        S  L  S  D  Y  G  V  H  W  V  R  Q  S  P  G  Q  G  L  E  C
        TCATTAAGCGACTATGGTGTTCAT TGGGTTCGCCAGTCTCCAGGACAGGGACTGGAGTGC 50  52 a       CDR2                    60
        L  G  V  I  W  A  G  G  G  T  N  Y  N  S  A  L  M  S  R  K
        CTGGGAGTAATATGGGCTGGTGGAGGCACGAATTATAATTCGGCTCTCATGTCCAGAAAG 70                          80    82 a  b
        S  I  S  K  D  N  S  K  G  Q  V  F  L  K  M  K  S  L  Q  A
        AGCATCAGCAAAGACAACTCCAAGGGCCAAGTTTTCTTAAAAATGAAGAGTCTGCAAGCT 90              CDR3         100 a  b  c  d
        D  D  T  A  V  Y  Y  C  A  R  D  K  G  Y  S  Y  Y  Y  S  M
        GATGACACAGCCGTGTATTACTGTGCCAGAGATAAGGGATACTCCTATTACTATTCTATG 110
        D  Y  W  G  Q  G  T  S  V  T  V  S  S  D
        GACTACTGGGGTCAAGGAACCTCAGTCACCGTCTCCTCTGATCA
            "JH4"                                  BclI
```

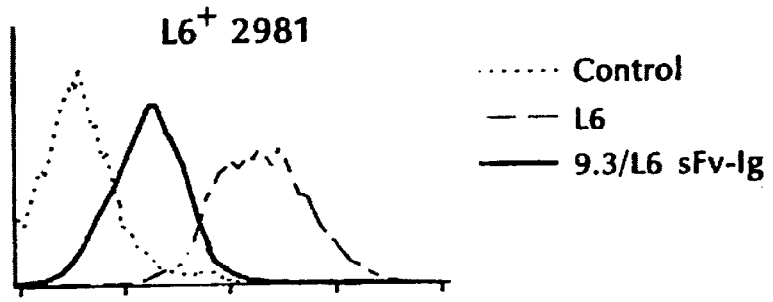
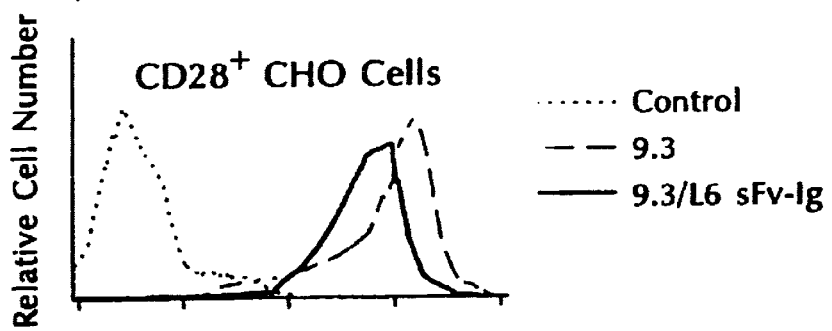
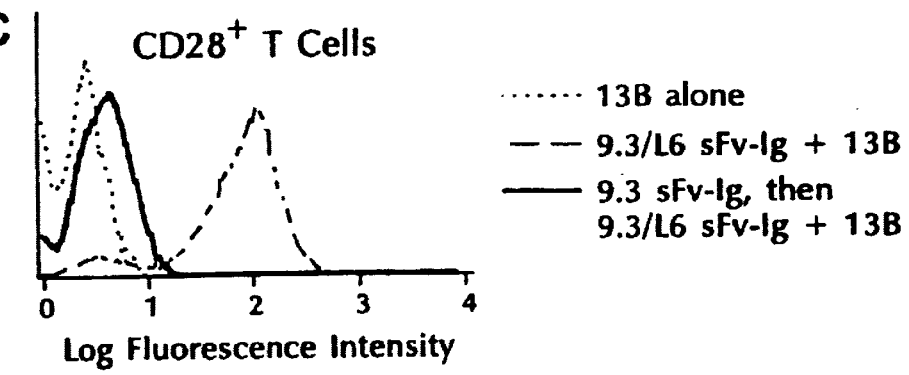

US 6,699,715 B1

MODIFIED SFV MOLECULES WHICH MEDIATE ADHESION BETWEEN CELLS AND USES THEREOF

This application is claiming the benefit of provisional application U.S. Ser. No. 60/007,755, filed Nov. 30, 1995 which is incorporated by reference herein. Throughout this application various publications are referenced. The disclosures of these publications in their entireties are hereby incorporated by reference into this application in order to more fully describe the state of the art to which this invention pertains.

The present invention relates to modified sFv molecules and uses thereof. The modified sFv molecules of the invention mediate adhesion between cells and comprise a binding site of an antibody and a transmembrane domain of a cell surface receptor.

BACKGROUND OF THE INVENTION

Naive CD4+ T-cells require two independent signals in order to be successfully activated and capable of undergoing clonal expansion (Janeway, Cold Spring Harbor Symp. Quant. Biol. 54:1–14 (1989)). The first signal is achieved by stimulation through the T-cell receptor by immunogenic peptides presented by MHC class II molecules on antigen presenting cells (APC) (Weiss, J. Clin. Invest. 86:1015 (1990)).

In addition, a second signal, referred to as costimulation, is also required. This costimulatory signal is generally provided through the ligation of CD28 on the T-cell and its inducible counter-receptor CD80, or CD86 on the APC (Linsley et al, J. Exp. Med. 173:721–730 (1991)).

The modified single chain Fv (sFv) molecules of the invention, when expressed on a cell surface, act as artificial co-stimulatory ligands. They were constructed to enhance an immune response to disease.

Others have constructed sFv molecules for purposes of intracellular targeting to combat disease (Biocca and A. Cattaneo, (1995) Trends in Cell Biology 5:248–252). However, the sFv molecules so constructed did not comprise a transmembrane domain which could be anchored to an extracellular surface (Biocca and Cattaneo, supra).

sFv molecules are one example of a myriad of molecules that are being tested for potential therapeutic and diagnostic uses against disease. Additional molecules of this type are needed.

SUMMARY OF THE INVENTION

The modified sFv molecules of the present invention stimulate adhesion between cells thereby enhancing an immune response against disease. These molecules generally comprise a binding site of an antibody and at least a portion of a transmembrane domain of a cell surface receptor.

In one embodiment of the invention, the modified sFv molecule further comprises a linker which connects the binding site to at least a portion of the transmembrane domain. In a specific embodiment, the modified sFv molecule comprises a binding site which recognizes and binds the CD28 receptor, a Fc portion of an antibody, and at least a portion of a transmembrane domain. In this embodiment, the binding site has two variable regions ($V_H$ and/or $V_L$ chains) and the Fc portion connects the binding site with the transmembrane domain.

BRIEF DESCRIPTION OF THE FIGURES

FIGS. 10A and 10B provide a nucleic acid sequence of a modified sFv encoded by PLNC-2e12hIgG1hB7-1Tm.

FIGS. 11A and 11B provide a nucleic acid sequence of a modified sFv encoded by PLNC-2e12hIgG1CD58GPI.

FIG. 12A provides a nucleic acid sequence (SEQ ID NO: 31) of the 2E12 sFv having the starting and ending sequences shown.

FIGS. 12B–D provides nucleic acid (SEQ ID NO: 32) and amino acid (SEQ ID NO: 33) sequences of the Fc portion of an antibody, namely, human IgG1, having the starting and ending sequences shown.

FIG. 12E provides a nucleic acid sequence of the B7-1 transmembrane domain (SEQ ID NO: 35).

FIG. 12F provides a nucleic acid sequence (SEQ ID NO: 37) and amino acid sequence (SEQ ID NO: 36) of CD58 GPI.

FIG. 13 provides the nucleotide sequence (SEQ ID NO: 38) and "amino acid sequence" (SEQ ID NO: 39) of the 9.3 $V_L$ and $V_H$ and the gene fusion created in the sFv. The restriction sites used for subcloning the sFv are shown at each end of the sequence, and the 9.3 native leader sequence for the light chain is boxed and labeled. The complementarity determining regions (CDR) are also boxed and labeled. The $V_L$ is most homologous to the murine kappa III V-region family as defined by Kabat et al. (Sequences of proteins of immunological interest. 45th edition. Bethesda, Md.; Public Health Service, National Institutes of Health, 1987)) and the V gene segment has rearranged with a J gene segment homologous to murine Jk2 (underlined and labeled). The $V_H$ is most homologous to the B subfamily of the murine I V region family. The heavy chain V gene has rearranged with a J gene segment homologous to murine JH4 (underlined and labeled).

FIG. 14 is a photograph of a Western blot of culture supernatants from COS cells. COS cell supernatants (100 ml) from mock transfected cells (Lane 1) L6 sFvIg (Lane 2), 9.3 sFvIg (Lane 3), and 9.3/L6 sFvIg (Lane 4) were immunoprecipitated with 50 μl Staphylococcus protein A beads, washed, boiled in loading buffer, and subjected to SDS-PAGE using 6–15% gradient gels. Gels were blotted to nitrocellulose and incubated with alkaline phophatase conjugated goat anti-human IgG to visualize proteins. The L6 and 9.3 sFvIg proteins migrate at $M_r$ 55,000, the 9.3/L6 sFvIg proteins migrate at $M_r$ 83,000, the approximate size expected for these fusion proteins.

FIGS. 15a/b/c are line graphs showing that the bispecific 9.3/L6 sFvIg fusion protein binds to L6+ H2981 tumor cells and to CD28+ CHO cells. Panel 15A: L6+ H2981 tumor cells were incubated with L6 sFvIg ( - - - - ) at 0.5 μg/ml or 9.3 sFvIg ( . . . . ) at 0.5 μg/ml or 9.3/L6 sFvIg (_____) fusion protein at 0.5 μg/ml or with medium alone ( . . . . ). Panel 15B: CD28 CHO cells were incubated with 9.3 sFvIg ( - - - - ) at 1 μg/ml or 9.3/L6 sFvIg fusion protein (_____) at 1 μg/ml, or with medium alone ( . . . . ). Bound protein was detected with FITC conjugated goat anti-human IgG at 1:100. Panel 15C: CD28+ PHA blasts were incubated with FITC conjugated L6 α-idiotype mAb 13B ( . . . . ) as negative control, bispecific 9.3/L6 sFvIg at 0.5 μg/ml and bound protein detected with FITC conjugated L6 α-idiotypic mAb 13B ( - - - - ). Preincubation of cells with unlabelled 9.3 sFvIg inhibited binding of bispecific 9.3/L6 sFvIg as shown by a significant reduction in FITC-13B staining (_____). A total of 10,000 cells were analyzed per sample.

DETAILED DESCRIPTION OF THE INVENTION

Definition

Figure 1A:
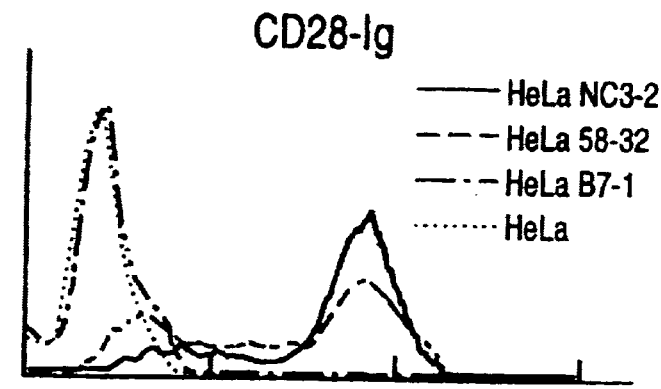
FIG. 1 is a FACS analysis of Hela cells infected with retroviral constructs NC3-2 (_____), 58-32 ( - - - - ), B7-1 (also known as CD80) ( · - · · - · - ), or non-infected cells ( . . . . ). Hela cells infected with the 58-32 or NC3-2 retroviruses express the 2E12 sFv on the cell surface as detected either by binding to CD28 or by binding to anti-human Ig. The Hela cells infected with the B7-1 (CD80) retrovirus express high levels of B7-1 (CD80).

As used in this application, the following words or phrases have the meanings specified.

As used herein a "modified sFv molecule" is a recombinantly produced antibody fragment comprising a binding site of an antibody and a transmembrane domain of a cell surface receptor or portion thereof. So long as the binding function of the molecule is preserved, the modified sFv molecules can include additional amino acid sequences linked to either its C- or N-terminus and the nucleic acid molecules encoding the modified sFv molecules can include additional nucleotides to its 5' or 3'-terminus.

As used herein a "binding site" means the portion of the molecule which recognizes and binds a target. The binding site includes one or more variable regions.

As used herein "variable region" means a variable heavy ($V_H$) chain or a variable light ($V_L$) chain, in its entirety or portion thereof which recognizes and binds its target.

As used herein "leucocyte antigen" includes any cell surface receptor having a transmembrane domain and found on a leucocyte.

As used herein a "transmembrane domain" means that portion of a cell surface receptor that anchors the receptor to the membrane or transits a membrane. The transmembrane domain can include a cytoplasmic region (also known as a cytoplasmic tail). The cytoplasmic region may or may not have signaling capabilities, i.e., the capability to interact with cytoplasmic components that are directly or indirectly involved in the transduction of the antigen binding signal.

As used herein "at least a portion of a transmembrane domain" means any portion of the transmembrane domain that serves to anchor the cell surface receptor to the cell membrane. It is that portion of the transmembrane domain that spans the whole width of a membrane or any part thereof thereby serving to anchor the cell surface receptor to the cell membrane.

As used herein a "linker" means any molecule that links the binding site to the transmembrane domain.

In order that the invention herein described may be more fully understood, the following description is set forth.

Modified SFV Molecules of the Invention

The present invention provides modified sFv molecules which serves as artificial adhesion receptors. These molecules can mediate adhesion between lymphocytes These molecules can also mediate adhesion between lymphocytes and non-lymphocytic cells.

Typically, the modified sFv molecule of the invention comprises a binding site of an antibody and at least a portion of a transmembrane domain of a cell surface receptor. The binding site can have one or more variable regions. Two variable regions are preferable, e.g., $V_H$ and $V_L$ chains.

The transmembrane domain can include a cytoplasmic region of a cell surface receptor. The cytoplasmic region can be in its entirety or a portion thereof. It may or may not exhibit signalling capabilities. The cytoplasmic region may be from the same cell surface receptor as the transmembrane domain or from a different cell surface receptor. The cytoplasmic region can contain activation sequences such as antigen receptor homology 1 (ARH1) or enzymatic domains such as protein tyrosine kinase (PTK) or protein tyrosine phosphatase (PTP).

In a further embodiment of the invention, the binding site recognizes and binds a first leucocyte antigen. Additionally, the transmembrane domain is from a second leucocyte antigen. The first and second leucocyte antigens may be the same or different. Preferably, the first leucocyte antigen is different from the second leucocyte antigen.

Examples of leucocyte antigens include, but are not limited to, CD1, CD2, CD3/TCR, CD4, CD5, T12, CD7, CD8, CD9, CD10, CD11, CD13, CD14, CD15, CD18, CD19, CD20, CD21, CD22, CD23, CD24, CD25, CD26, CD27, CD28, CD29, CD30, CD31, CDw32, CD33, CD34, CD35, CD37, CD38, CD40, CD41, CD43, CD44, CD45, CD46, CD48, CD49, CDw50, CD51, CDw52, CD53, CD54, CD55, CD56, CD57, CD58, CD59, CDw60, CD61, CD62, CD63, CD64, CDw65, CD66, CD67, CD68, CD69, CDw70, CD71, CD72, CD73, CD74, CD75, CD76, CD77, CDw78, 4-1BB, 4F2, 114/A10, B7-1 (CD80), B7-2 (CD86), B-G, BP-1/6C3, C5aR, c-Kit, CMRF35 antigen, CTLA-4, endoglin, Fas, FcaR, FceRI, flk-2, fMLPR, G-CSFR, GM-CSFR, gp42, gp49, HSA, ICAM-2, IFNgR, IL1R, IL3R, IL4R, IL5R, IL6R, IL7R, IL8R, LAG-3, LDLR, L-Selectin, ltk, Ly-6, Ly-9, Ly-49, Mac-2, Mannose receptor, M-ASGP-BP, M-CSFR, MDR1, MHC Class I, MHC Class II, MIC2, mIgM, MRC OX-2, MRC OX-40, MRC OX-47, NKG2, NKR-P1, PC-1, R2, RT6, Scavenger RI and II, Syndecan, TAPA-1, Thy-1, and TNFRI and II.

In accordance with the practice of the invention, the first or second leucocyte antigen is CD28. Additionally, the first or second leucocyte antigen is B7 (CD80 or CD86). Further, the first or second leucocyte antigen is CTLA4.

In accordance with the practice of the invention, the modified sFv molecule may further comprise a linker. The linker connects the binding site to at least a portion of a transmembrane domain. Additionally, the linker can be useful as an identification tag for detection purposes.

A Fc portion of an antibody is one example of a linker. Another examples of a suitable linker is a helical peptide linker (Newton C R, et al., Cloning and expression in murine erythroleukemia cells: the soluble forms type I and type II tumor necrosis factor receptors fused to an immunogenic affinity tag. Protein Expression and Purification, 1994 October, 5(5):449–57). Additionally, The "tag" peptide -Ala-Ala-Asn-Asp-Glu-Asn-Tyr-Ala-Leu-Ala-Ala-COOH (SEQ ID NO: 1) is another example of a linker (Tu GF, et al, C-terminal extension of truncated recombinant proteins in Escherichia 10Sa RNA decapeptide. Journal of Biological Chemistry, Apr. 21, 1995 270(16):9322–6).

Another suitable linker is the hinge-like region of B7-1 or B7-2. A peptide segment or a second functional domain such as an Ig, a growth hormone, an adhesion receptor, or another sFv or part thereof are examples of suitable linkers.

Further, the FLAG sequence DYKDDDDK (SEQ ID NO: 2) is an example of a linker (Knappik A; Pluckthun A., An improved affinity tag based on the FLAG peptide for the detection and of recombinant antibody fragments. Biotechniques, Oct. 17, 1994 (4):754–61). Further, another example of a linker is the. Flag peptide consisting of the 11-amino-acid leader peptide of the gene product from bacteriophage T7 (Witzgall R, et al, A mammalian expression vector for the expression of GAL4 fusion proteins with an epitope tag and histidine tail. Analytical Biochemistry, 1994 December, 223(2):291–8).

The "Strep tag" is yet another example of a linker (Schmidt T G; Skerra A., One-step affinity purification of bacterially produced proteins by means of the "Strep tag" and immobilized recombinant core streptavidin. Journal of Chromatography a, Aug. 5, 1994 676(2):337–45).

The influenza virus hemagglutinin (HA) epitope tag is an example of a linker (Chen Y T, et al, Expression and localization of two low molecular weight GTP-binding proteins, Rab8 and Rab10, by epitope tag. PNAS, Jul. 15, 1993 90(14):6508–12).

A 14-amino acid oligopeptide in simian virus 5 (SV5) is still another example of a linker (Hanke T, et al, Construction of solid matrix-antibody-antigen complexes containing simian immunodeficiency virus p27 using tag-specific monoclonal antibody and tag-linked antigen. Journal of General Virology, 1992 March, 73 (Pt 3):653–60).

Also, the sequence Ala-Leu-Ala-Leu (SEQ ID NO: 3) is an example of a linker (Studer M, et al, Influence of a peptide linker on biodistribution and metabolism of antibody-conjugated benzyl-EDTA. Comparison of enzymatic digestion in vitro and in vivo. Bioconjugate Chemistry, 1992 September–October, 3(5):424–9).

The myc epitope is another example of a linker (Simons M, et al, Intracellular routing of human amyloid protein precursor: axonal delivery transport to the dendrites. Journal of Neuroscience Research, May 1, 1995 41(l):121–8).

The seven-histidine tag is another example of a linker (Parks T D, et al, Expression and purification of a recombinant tobacco etch virus NIa proteinase: biochemical analyses of the full-length and a naturally occurring truncated proteinase form. Virology, Jun. 20, 1995 210(1):194–201; Vouret-Craviari V, et al, Post-translational and activation-dependent modifications of the G protein-coupled thrombin receptor. Journal of Biological Chemistry, Apr. 7, 1995 270(14):8367–72).

The synthetic peptide based on the amino acid sequence of the C terminal region of native human factor X activation peptide (FXAP) is another example of a linker (Philippou H, et al, An ELISA for factor X activation peptide: application to the investigation of thrombogenesis in cardiopulmonary bypass. British Journal of Haematology, 1995 June, 90(2):432–7).

Another linker is the small antigenic peptide epitope (YPYDVPDYAIEGR) (SEQ ID NO: 4) containing part of the hemagglutinin (HA) of influenza virus (Kast C, et al, Membrane topology of P-glycoprotein as determined by epitope insertion: transmembrane organization of the N-terminal domain of mdr3. Biochemistry, Apr. 4, 1995 34(13):4402–11).

The epsilon-tag peptide is another linker (Lehel C, et al, Protein kinase C epsilon is localized to the Golgi via its zinc-finger modulates Golgi function. PNAS, Feb. 28, 1995 92(5):1406–10).

The KGF-SYFGEDLMP (SEQ ID NO: 5) peptide is another linker. This sequence is derived and is encoded by the tagging insert sequence of Olah Z, et al, A cloning and epsilon-epitope-tagging insert for the expression of polymerase chain reaction-generated cDNA fragments in Escherichia coli and mammalian cells. Analytical Biochemistry, Aug. 15, 1994 221(1):94–102.

Another linker is the six histidine tag (Sporeno E, et al, Production and structural characterization of amino terminally histidine tagged human oncostatin M in *E. coli*. Cytokine, 1994 May, 6(3):255–64).

The streptavidin-affinity tag is also an example of a linker (Schmidt T G; Skerra A., The random peptide library-assisted engineering of a C-terminal affinity peptide, useful for the detection and purification of a functional Ig Fv fragment. Protein Engineering, 1993 January, 6(l):109–22).

The hemagglutinin epitope sequence, YPYDVPDYA (HA1) (SEQ ID NO: 6) is yet another example of a linker (Pati U K., Novel vectors for expression of cDNA encoding epitope-tagged proteins in mammalian cells. Gene, May 15, 1992 114(2):285–8).

Preferably, the linker should not exhibit cross reactivity with the binding site for the ligand. Further, the linker should not recognize and bind the binding site. For example when the binding site recognizes and binds the CD28 receptor, the linker cannot be the CD28 receptor or parts thereof.

The linker may provide structural support, functional support, or both. For example, the Fc linker provides effector functions as well as structural function, i.e., in connecting the binding site of the molecule to the transmembrane domain.

One example of the invention includes a modified sFv molecule comprising a binding site of an antibody which recognizes and binds the CD28 receptor (e.g., the 2E12 sFv encoded by the nucleic acid sequence (shown in FIG. 12A) or the binding site of the 9.3 antibody), a Fc portion of an antibody, and at least a portion of a transmembrane domain and cytoplasmic tail of the B7 receptor. Like 2E12 sFv, the 9.3 monoclonal antibody (mAb) recognizes and binds the CD28 receptor (ATCC No. HB 10271, Hansen et al., *Immunogenetics* 10:247–260 (1980); Parham, et al. *J. Immunol.* 131:2895–2902 (1983)).

In comparison with CD80, a natural adhesion receptor for CD28, the 2E12 sFv showed increased binding affinity for CD28 and was efficient in activating T cells during co-culture. Because of these characteristics, the cell surface expression of modified sFv molecules offer advantages over natural ligands for binding and activation of adhesion receptors.

In another embodiment, the invention provides a modified sFv molecule comprising a binding site of an antibody which recognizes and binds the CD28 receptor, a Fc portion of an antibody, and at least a portion of a transmembrane domain which is a CD58 GPI tail.

Other modifications to the sFv molecules of the invention are possible. These modifications include the addition of protein or peptide segments or modification of existing segments which would enhance the molecules' ability to mediate adhesion between cells. Additionally, these modifications involve amino acid substitutions within the molecule. These substitutions include, but are not necessarily limited to, amino acid substitutions known in the art as "conservative".

For example, it is a well-established principle of protein chemistry that certain amino acid substitutions, entitled "conservative amino acid substitutions," can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa.

Other substitutions can also be considered conservative, depending on the environment of the particular amino acid and its role in the three-dimensional structure of the protein. For example, glycine (G) and alanine (A) can frequently be interchangeable, as can alanine and valine (V).

Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. Still other changes can be considered "conservative" in particular environments.

Nucleic Acid Molecules, Vectors and Host Vector Systems for Making the Modified SFV Molecules of the Invention The present invention also provides nucleic acid molecules (such as DNA molecules) encoding the modified sFv molecules of the invention. In one example, the DNA is cDNA having the sequence shown in FIGS. 10A and 10B. Additionally, the cDNA has the sequence shown in FIGS. 11A and 11B. FIG. 12A shows an example of the 5'-portion of a nucleic acid molecule according to the present invention, encoding 2E12. FIGS. 12B–12D show the nucleic acid sequence of the central portion of a nucleic acid molecule according to the present invention, encoding a portion of IgG1; this portion acts as a linker. FIG. 12E shows the nucleic acid sequence of the 3'-portion of a nucleic acid molecule according to the present invention, encoding the transmembrane domain of B7-1 (CD80). In another alternative, FIG. 12F shows the nucleic acid sequence of GPI, which can be used as the nucleic acid sequence of the 3'-portion of a nucleic acid molecule according to the present invention.

Nucleic acid molecules include both DNA and RNA unless otherwise indicated, and can include both single and double-stranded nucleic acid sequences. If a DNA sequence is referred to, reference is generally to both strands of a DNA sequence, either individually or as a Watson-Crick double helix. If only one strand is specified, the complementary strand whose antiparallel sequence is determined by Watson-Crick base pairing rules is also included unless the complementary sequence is specifically excluded. If only one strand is specified in double-stranded -DNA, the strand specified is the sense strand, and is the strand that would be equivalent to the sequence of any RNA transcribed from the double-stranded DNA, except for the replacement of thymidine (T) in the DNA by uridine (U) in the RNA. Reference to a nucleic acid sequence also includes-modified bases as long as the modification does not significantly interfere with Watson-Crick base pairing or other specified functions of the nucleic acid, and can, for example, include substitution of uridine for thymidine in DNA as well as methylation of bases or modification of sugars.

Further, producer cells transfected with such nucleic acid molecules are provided.

Figure 7:
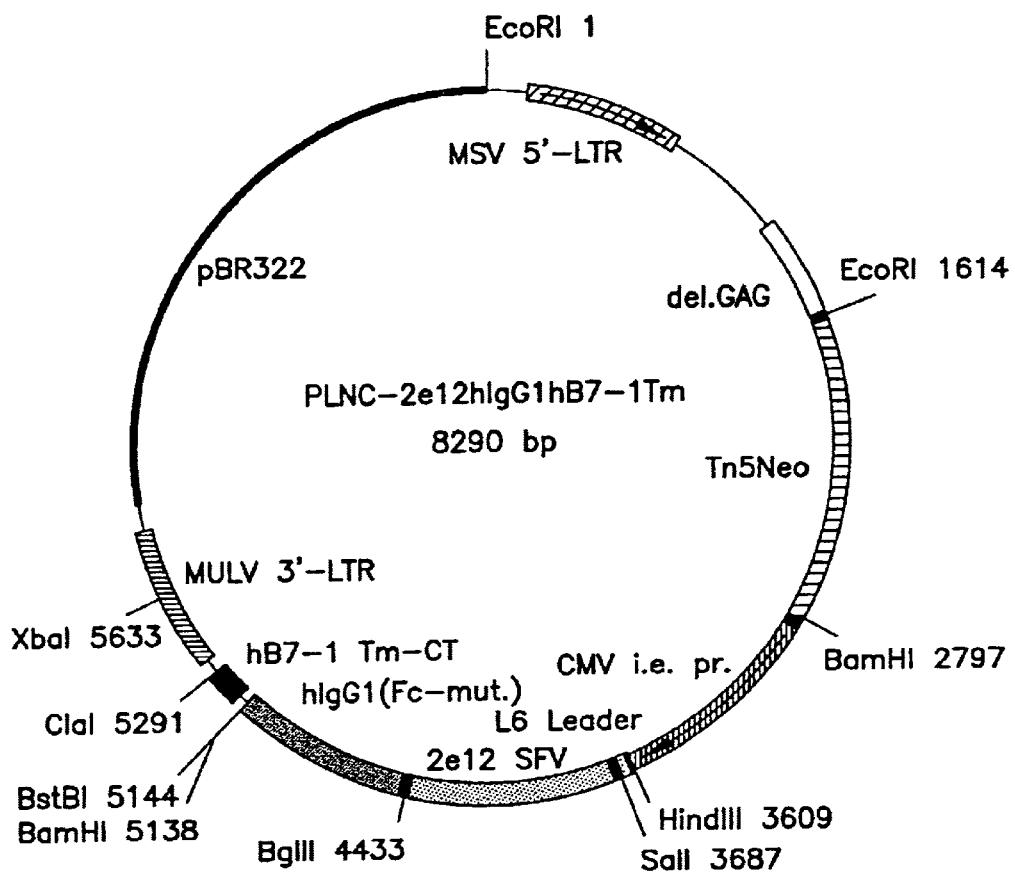
FIG. 7 is a diagram of plasmid PLNC-2e12hIgG1hB7-1Tm.
Figure 8:
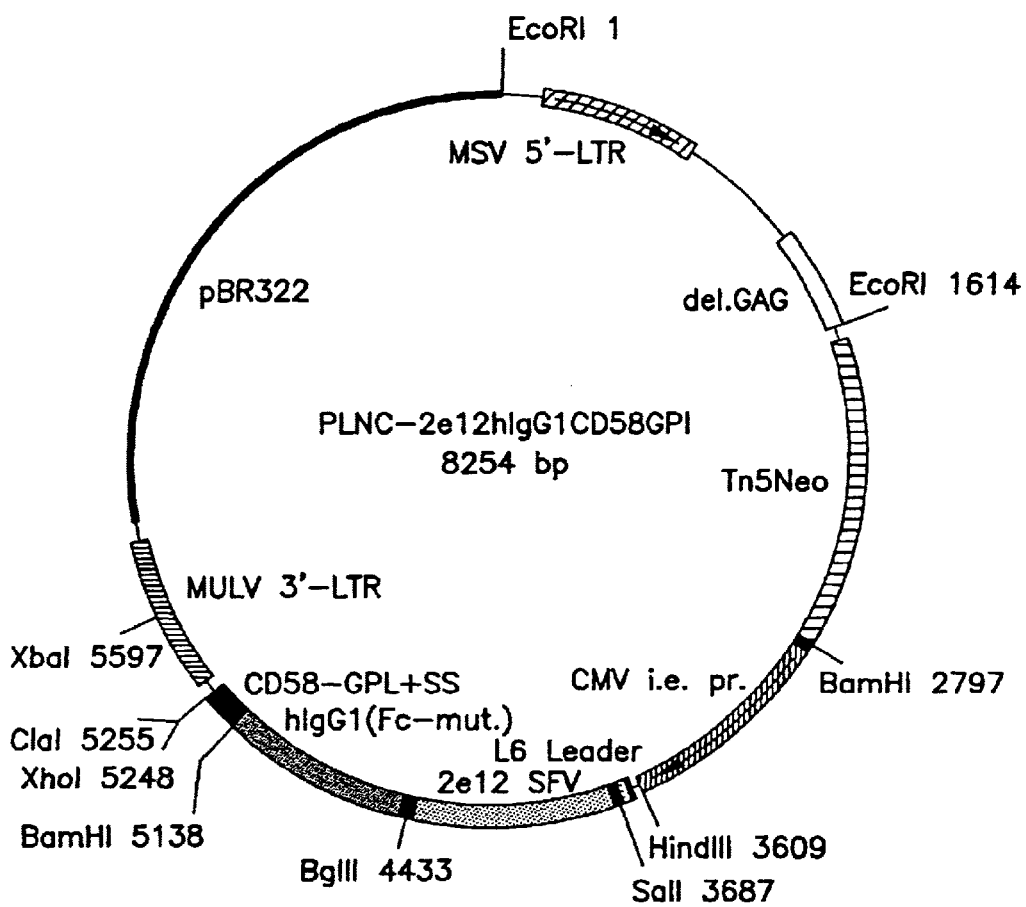
FIG. 8 is diagram of plasmid PLNC-2e12hIgG1CD58GPI.

The subject invention further provides an expression vector encoding the sFv molecule of the invention. In one embodiment, the expression vector is designated pLNC-2e12-hIgG1-hB7-1Tm (FIG. 7). Alternatively, the expression vector is designated pLNC-2e12-hIgG1-hCD58GPI (FIG. 8).

The invention further provides a eucaryotic cell transfected with the expression vector of the invention. In one example, the eucaryotic cell is a mammalian cell. Examples include but are not limited to Hela cells, NIH 3T3 cells, and tumor cells such as H334-7 (L6+) and H3396 (BR96+).

Methods of Using the Modified SFV Molecules and Vectors Encoding Them

The invention also provides methods for producing the modified sFv molecules of the invention. In one embodiment, the method comprises culturing the cells transfected by the expression vector of the invention so as to produce the modified sFv molecules and recovering the molecules so produced.

In another embodiment, the invention provides a method for producing modified sFv molecules in a mammalian cell. This method comprises transfecting the mammalian cell with the expression vector of the invention; culturing the mammalian cell so transfected; and recovering the modified sFv molecules so produced by the cultured mammalian cell.

In accordance with the practice of the invention, the step of recovering the biologically active sFv molecule comprises (a) identifying the modified sFv molecule (e.g., by the presence of the binding site or the transmembrane domain); and (b) separating the modified sFv molecule so identified from non-identified molecules, so as to recover the modified sFv molecule so produced by the cultured mammalian cell.

The present invention further provides a method for enhancing a T cell response in a subject. The methods include an ex vivo protocol and an in vivo protocol.

In one embodiment of the ex vivo protocol, the method comprises administering autologous donor cells (e.g., peripheral blood leukocytes (PBLs)) into the subject. In this embodiment, the PBLs are incubated in vitro with the mammalian cells of the invention. The mammalian cells are genetically modified to express modified sFv molecules to its cell surface thereby providing a co-stimulatory molecule for the PBLs. Incubation lasts for a sufficient time for the PBLs to stimulate a T cell response. Post-incubation, the activated PBLs are administered to the subject.

In another embodiment of the ex vivo protocol, the cells can be autologous or allogeneic cells, e.g., PBLs, tumor cells, or tumor infiltrating lymphocytes (TILs).

Allogeneic cells can be encapsulated in order to prevent or inhibit an immune response. Alternatively, the allogeneic cells can be irradiated. Further alternatively, the subject may be administered with an immunosuppressant agent to prevent or inhibit an immune response.

These cells, whether autologous or allogeneic, are genetically modified by insertion of the expression vector of the invention into the cells so as to produce modified sFv molecules attached to the cell surface in a sufficient amount so as to stimulate a T cell response once in the subject and thereby inhibiting tumor growth in the subject.

In one embodiment of the in vivo protocol, the method comprises introducing nucleic acid molecules of the invention or transfection vehicles containing such nucleic acid molecules e.g., a vector, into a producer cell of the invention. Various methodologies for introducing the vector into the producer cells and further examples of transfection vechicles are found infra.

The vector contains DNA encoding the modified sFv molecule of the invention and at least one gene required- for replication of the retrovirus into the genome of the producer cells.

In this in vivo protocol, the method further comprises the step of selecting producer cells in which the modified retrovirus is incorporated as part of the genome of the producer cells. The producer cells so selected are then administered in proximity to the tumor cells in order to infect the tumor cells with the modified vector being produced by the producer cells, thereby transferring the DNA to the tumor cells.

In accordance with the practice of the invention, the subject may be an animal subject such as a human, a dog, a cat, a sheep, a horse, a fish, a bird, a pig, or a cow.

Presently, several groups are using gene therapy in cancer treatment (Friedmann T. Progress toward human gene therapy. Science 1989; 244:1275–1281; Roth J A, et al. Molecular approaches to prevention and therapy of aerodigestive tract cancers. Review article. Monogr Natl Cancer Inst 1992; 13:15–21; Mukhopadhyay T, et al. Specific inhibition of K-ras expression and tumorigenicity of lung cancer cells by antisense RNA. Cancer Res 1991; 51:1744–1748).

The most effective mode of administration and dosage regimen for the molecules of the present invention depends upon the location of the tissue or disease being treated, the severity and course of the medical disorder, the subject's health and response to treatment and the judgment of the treating physician. Accordingly, the dosages of the molecules should be titrated to the individual subject.

The interrelationship of dosages for animals of various sizes and species and humans based on $\mu g/m^2$ of surface area is described by Freireich, E. J., et al. Cancer Chemother., Rep. 50 (4): 219–244 (1966). Adjustments in the dosage regimen may be made to optimize the tumor cell growth inhibiting and killing response, e.g., doses may be divided and administered on a daily basis or the dose reduced proportionally depending upon the situation (e.g., several divided doses may be administered daily or proportionally reduced depending on the specific therapeutic situation).

It would be clear that the dose of the composition of the invention required to achieve cures may be further reduced with schedule optimization.

Introduction of Vectors or Nucleic Acid Molecules of the Invention Into Cells A variety of techniques are available for the introduction of nucleic acid molecules into cells. For example, the nucleic acid molecule may be inserted into a cell directly in a recombinant viral vector. Other insertion methods are possible.

For example, in ex vivo techniques, the gene can be inserted into a cell using any gene transfer procedure such as calcium phosphate mediated transfection, the use of polycations or lipids complexed with DNA, encapsulation of DNA in lipid vesicles or erythrocyte ghosts, or the exposure of cells to rapid pulses of high voltage electric current (i.e., electroporation).

DNA has also been introduced into cells by direct microinjection or by the use of high-velocity tungsten microprojectiles. These techniques are capable of integrating multiple copies of DNA into the genome although the efficiency of the integration varies widely with the technique, different genes, and different cell types.

Recently techniques have been developed using viral vectors to introduce DNA into mammalian cells. These techniques have the potential for infecting all cells exposed to the virus. In developing techniques for the use of viral vectors, it was necessary to develop vectors that stably incorporated into the target cell without damaging it.

Suitable viral vectors include papovaviruses, simian virus 40, polyomavirus, adenoviruses, murine and avian retroviruses. Viral vectors can infect multiple cell types.

Compared to vectors that do not enter cells by receptor mediated events, viral vectors are preferred because of their efficiency. Examples of suitable viral vectors include, but are not limited to, a retrovirus vector, an adenovirus vector, a vaccinia virus vector, a herpes virus vector, or a rabies virus vector.

The viral vector selected should meet the following criteria: 1) the vector must be able to infect the cells of interest and thus viral vectors having an appropriate host range must be selected; 2) the transferred gene should be capable of persisting and being expressed in a cell for an extended period of time; and 3) the vector should be safe to the host and cause minimal cell transformation. Retroviral vectors and adenoviruses offer an efficient, useful, and presently the best-characterized means of introducing and expressing foreign genes efficiently in mammalian cells.

These vectors have very broad host and cell type ranges, express genes stably and efficiently. The safety of these vectors has been proved by many research groups. In fact many are in clinical trials.

Other virus vectors that may be used for gene transfer into cells for correction of disorders include herpes virus papovaviruses such as JC, SV40, polyoma; Epstein-Barr Virus (EBV); papilloma viruses, e.g. bovine papilloma virus type I (BPV); poliovirus and other human and animal viruses.

Adenoviruses have several properties that make them attractive as cloning vehicles (Bachettis et al.: Transfer of gene for thymidine kinase-deficient human cells by purified herpes simplex viral DNA. *PNAS USA*, 1977 74:1590; Berkner, K. L.: Development of adenovirus vectors for expression of heterologous genes. *Biotechniques*, 1988 6:616; Ghosh-Choudhury G, et al., Human adenovirus cloning vectors based on infectious bacterial plasmids. *Gene* 1986; 50:161; Hag-Ahmand Y, et al., Development of a helper-independent human adenovirus vector and its use in the transfer of the herpes simplex virus thymidine kinase gene. *J Virol* 1986; 57:257; Rosenfeld M, et al., Adenovirus-mediated transfer of a recombinant $a_1$-antitrypsin gene to the lung epithelium in vivo. *Science* 1991; 252:431).

For example, adenoviruses possess an intermediate sized genome that replicates in cellular nuclei; many serotypes are clinically innocuous; adenovirus genomes appear to be stable despite insertion of foreign genes; foreign genes appear to be maintained without loss or rearrangement; and adenoviruses can be used as high level transient expression vectors with an expression period of weeks to several months. Extensive biochemical and genetic studies suggest that it is possible to substitute up to 7–7.5 kb of heterologous sequences for native adenovirus sequences generating viable, conditional, helper-independent vectors (Kaufman R. J.; Identification of the component necessary for adenovirus translational control and their utilization in cDNA expression vectors. *PNAS USA*, 1985 82:689).

AAV is a small human parvovirus with a single stranded DNA genome of approximately 5 kb. This virus can be propagated as an integrated provirus in several human cell types. AAV vectors have several advantage for human gene therapy. For example, they are trophic for human cells but can also infect other mammalian cells; (2) no disease has been associated with AAV in humans or other animals; (3) integrated AAV genomes appear stable in their host cells; (4) there is no evidence that integration of AAV alters expression of host genes or promoters or promotes their rearrangement; (5) introduced genes can be rescued from the host cell by infection with a helper virus such as adenovirus.

HSV-1 vector system facilitates introduction of virtually any gene into non-mitotic cells (Geller et al. An efficient deletion mutant packaging system for a defective herpes simplex virus vectors: Potential applications to human gene therapy and neuronal physiology. *PNAS USA*, 1990 87:8950).

Another vector for mammalian gene transfer is the bovine papilloma virus-based vector (Sarver N, et al., Bovine papilloma virus DNA: A novel eukaryotic cloning vector. *Mol Cell Biol* 1981; 1:486).

Vaccinia and other poxvirus-based vectors provide a mammalian gene transfer system. Vaccinia virus is a large double-stranded DNA virus of 120 kilodaltons (kd) genomic size (Panicali D, et al., Construction of poxvirus as cloning vectors: Insertion of the thymidine kinase gene from herpes simplex virus into the DNA of infectious vaccine virus. *Proc Natl Acad Sci USA* 1982; 79:4927; Smith et al. infectious vaccinia virus recombinants that express hepatitis B virus surface antigens. *Nature*, 1983 302:490.)

Retroviruses efficiently insert viral genes into host cells (Guild B, et al., Development of retrovirus vectors useful for expressing genes in cultured murine embryonic cells and hematopoietic cells in vivo. *J Virol* 1988; 62:795; Hock R A, et al., Retrovirus mediated transfer and expression of drug resistance genes in human hemopoietic progenitor cells. *Nature* 1986; 320:275; Kriegler M. Gene transfer and expression. A laboratory manual. New York: Stockton Press, 1990:1–242; Gilboa E, Eglitis M A, Kantoff P W, et al. Transfer and expression of cloned genes using retroviral vectors. Biotechniques 1986; 4:504–512; Eglitis A M, Anderson W F. Retroviral vectors for introduction of genes into mammalian cells. Biotechniques 1988; 6:608–614; Adam M A, Miller A D. Identification of a signal in a murine retrovirus that is sufficient for packaging of nonretroviral RNA into virions. J Virol 1988; 62:3802–3806; Armentano D, Yu S F, Kantoff P W, et al. Effect of internal viral sequences on the utility of retroviral vectors. J Virol 1987; 61:1647–1650; Bender M A, Palmer T D, Gelinas R E, et al. Evidence that the packaging signal of Moloney murine leukemia virus extends into the gag region. J Virol 1987; 61:1639–1646; Danos O, Mulligan R C. Safe and efficient generation of recombinant retroviruses with amphotropic and ecotropic host ranges. Proc Natl Acad Sci USA 1988; 85:6460–6464; Markowitz D, Goff S, Bank A. Construction and use of a safe and efficient amphotropic packaging cell line. Virol 1989; 167:400–406; Miller A D, Buttimore C. Redesign of retrovirus packaging cell lines to avoid recombination leading to helper virus production. Mol Cell Biol 1986; 6:2895–2902; Miller A D, Trauber D R, Buttimore C. Factors involved in the production of helper virus-free retrovirus vectors. Somatic Cell Mol Genet 1986; 12:175–183; Miller A D, Rosman G J. Improved retroviral vectors for gene transfer and expression. Biotechniques 1989; 7:980–986).

ADVANTAGES OF THE INVENTION: The discovery herein lies in modifying sFv molecules by connecting a transmembrane domain to the antigen binding site of the molecule. This modification creates molecules, namely, artificial ligands, that can further enhance co-stimulatory activity during an immune response.

For example, tumor cells are not immunogenic when they do not express natural ligands (CD80 or CD86) for CD28. Therefore, the molecules of the invention act as artificial adhesion receptors thereby increasing the immunogenicity of tumor cells by increasing the expression of co-stimulatory molecules (such as CD80 or CD86).

This artificial ligand may have several potential advantages over the use of CD80 or CD86. For example, an sFv can have a higher binding affinity than the natural ligand, and therefore may generate a stronger signal. The transmembrane domain can also be chosen to maximize mobility on the cell surface, resulting in a CD28 ligand that has a higher potency than CD80 or CD86.

Further, previous studies have shown that CD28 and CTLA-4 can bind to both CD80 and CD86 and that under some conditions, the signal generated through CTLA-4 binding can be inhibitory. In contrast, cells transfected with an anti-CD28 sFv would only bind through CD28 and the inhibitory effects of CTLA-4 ligation would be eliminated.

The data herein shows that tumor recognition by T cells requires costimulatory signals through adhesion receptors, and suggests that the increased expression of certain leucocyte antigens (e.g., ligands which recognize and binds CD28) on the cell surface may be a desirable goal for tumor gene therapy.

The following examples are presented to illustrate the present invention and to assist one of ordinary skill in making and using the same. The examples are not intended in any way to otherwise limit the scope of the invention.

EXAMPLE 1

The mAb 1TE+ 19.8.2 2E12 was generated by R. S. Mittler (see FIG. 12A).

Construction of sFv's: Isolation of variable regions: RNA was isolated from hybridoma 2E12 Using Stratagene mRNA Isolation Kit (Stratagene, Torrey Pines) according to manufacturer's instructions. First strand synthesis was carried out with Stratagene First Strand Synthesis Kit and primers specific for isotype and constant region.

cDNA reactions were poly-G tailed using dGTP and terminal transferase (Stratagene, Torrey Pines), and G-tailed cDNA was used in PCR with a forward primer containing poly-C sequences and reverse primers specific for mouse variable region (primers contained restriction sites for cloning). PCR products were ligated into PUC19 and positive clones checked by DNA sequencing.

sFv Assembly: Variable light and heavy regions were joined in a single coding region by a $(Gly_4Ser)_3$ linker created by using overlap extension PCR. The VL-$V_H$ cassette was subsequently ligated into a modified PUC19 vector containing a mutant form of human IgG1 Fc, for use in purification and diagnostic analysis. Finally, the sFv-Ig construct was inserted into an adapted expression vector (CDM8) containing the anti-L6 immunoglobulin light chain leader sequence for secretion of fusion proteins. DNA from positive clones was used in transient COS transfections and supernatants were tested by FACS and Western blot analysis.

Construction of the retroviral vector pLNC-2e12-hIgG1-hB7-1Tm: The 2E12 sFv was obtained from R. Mittler as plasmid in MC1061p3 cells. The restriction map was verified and the 2E12 sFv DNA was amplified as a Hind-III/Bgl-II fragment using the primers S2e12SFV-3: (5'-GTGAATTCCAAGCTTCCACC ATG GAT TTT CAA GTG CAG ATT-3' (SEQ ID NO: 7) and A2e12SFV: 5'-A GTG CAG ATC TGA GGA GAC GGT GAC-3' (SEQ ID NO: 8). The indicated triplets correspond to open reading frames. The bases in boldface in A2e12SFV indicate the base changes introduced to convert the Bcl-I restriction site at the end of the $V_H$ domain of the original 2E12 sFv to a Bgl-II site.

PCR reactions were 30 cycles at: 94 C, 30 sec., 48 C, 1 min., 72 C, 3 min. After cleavage with Hind-III and Bgl-II and purification using a QIA-Quick cartridge, the fragment was ligated into the corresponding restriction sites in the pCDNA1-hIgG1(Fc-) vector. The resulting pCDNA1-2e12sFv-hIgG1(Fc-) construct was tested for production of transient expression of the soluble sFv-Ig by transfection into Cos cells.

Cells were stained with CD28mIg followed by goat-anti-mouse Ig FITC conjugate or with goat-anti-human IgFITC conjugate to verify the presence of the sFv and the human Ig domain respectively. Ten of ten tested clones were positive for both but negative for staining with CTLA4mIg, demonstrating that the original CTLA4 insert in the vector had been replaced by a functional 2E12 sFv.

Secretion of the 2e12sFv-hIgG1(Fc-) fusion protein was demonstrated by adsorption of cell culture supernate from transiently transfected cos cells on Protein A Sepharose, followed by SDS-gel electrophoresis. Immunoblotting with CD28mIg at 2.5 μg/ml followed by goat anti-mouse HRP conjugate at 1/10000 dilution demonstrated a weak signal at approx. 57 kd in all tested culture supernates from clones of the 2e12-hIgG1(Fc-) constructs. Clones e7 and e8 were used for further constructions.

For construction of subsequent transmembrane-anchored sFv constructs, the 2e12-hIgG1(Fc-) construct was prepared by PCR from the pCDNA-1hIgG1 vector as a Hind-III/BamH-I fragment with an open reading frame extending through the BamH-I site. The PCR primers used were S2e12SFV-3 (see above) and AIGG1BAM: 5'-CTG CAT CCG GAT CCG CTT TAC CCG GAG ACA GGG AGA GGC-3' (SEQ ID NO: 9). PCR was performed by 30 cycles at: 94 C, 30 sec., 72 C, 5 min.

The Hind-III and BamH-I cleaved PCR fragment was purified as above and ligated into the Hind-III and BamH-I cleaved vector pSFVDNA1. This vector is derived from pCDNA-1 by insertion into the Hind-III and Xba-I sites of a double stranded synthetic 77-mer, which creates the new sequence (from Hind-III to XbaI): 5'-a agc tGA ATT CCA AGC TTG CAT CAG ATC TCT CAT CTA GAG GTT CGG ATC CTT CGA ACC GCA GTC TCG AGC ATC GAT AGc tag a-3' (SEQ ID NO: 10). Lower case letters indicate bases from PCDNA-I.

This cloning linker destroys the flanking Hind-III and Xba-I sites, and introduces the following restriction sites: Eco-RI, Hind-III, Bgl-II, Xba-I, BamH-I, BstB-I, Xho-I and Cla-I and the amino acid (aa) sequence (from EcoR-I to Cla-I): NSKLASDLSSRGSDPSNRSLEHR-stop (SEQ ID NO: 11). Six pSFVDNA-1 clones of the Hind-III–BamH-I 2e12-hIgG1 (Fc-) fragment were tested for transient expression in Cos cells and for secretion of the fusion protein.

Clones 2V5, 7, 9, 11, 13 were positive in both tests, but clone 2V1 was negative in both. This fusion protein has the additional aa DPSNRSLEHR (SEQ ID NO: 12) attached to the C-terminus (from the BamH-I cloning site).

Next, the transmembrane and cytoplasmic domains from the human B7-1 (CD80) were attached at the BstB-I site 3' of the 2e12-Ig fusion protein gene in-pSFVDNA-1. The B7-1 gene fragment was amplified from cDNA using the primers SHB71TM: 5'-CTGCATCCGTTCG AAC CTG CTC CCA TCC TGG GCC A-3' (SEQ ID NO: 13) and AHB71TM: 5'-CAGCGTTGACTCGAGTATCGATTTA TAC AGG GCG TAC ACT TTC CCT T-3' (SEQ ID NO: 14).

Amplification conditions were 30 cycles at 94 C, 30 sec., 68 C, 1 min., 72 C, 2 min. The PCR product comprises aa 242–288 of human B7-1, on a 179 bp fragment. After cleavage with BstB-I and Xho-I the 154 bp fragment remaining was purified and ligated into BstB-I and Xho-I cleaved pSFVDNA-1 containing the 2e12-hIgG1(Fc-) (pooled 2V1, 5, 7, 9, 11, 13 as described above).

Four clones with the correct 154bp insert were screened for expression in Cos cells of protein reacting with goat anti-mouse Ig and CD28-mIg reagents. Two of these were positive in both tests (2VB7#5 and #12), while two were negative in both tests (2VB7#3 and #9). Clone pSFVDNA-1 2e12-hIgG1(Fc-)-hB7-1Tm 2VB7#5 was used for the subsequent subcloning of the transmembrane anchored sFv into a retrovirus vector.

Figure 6:
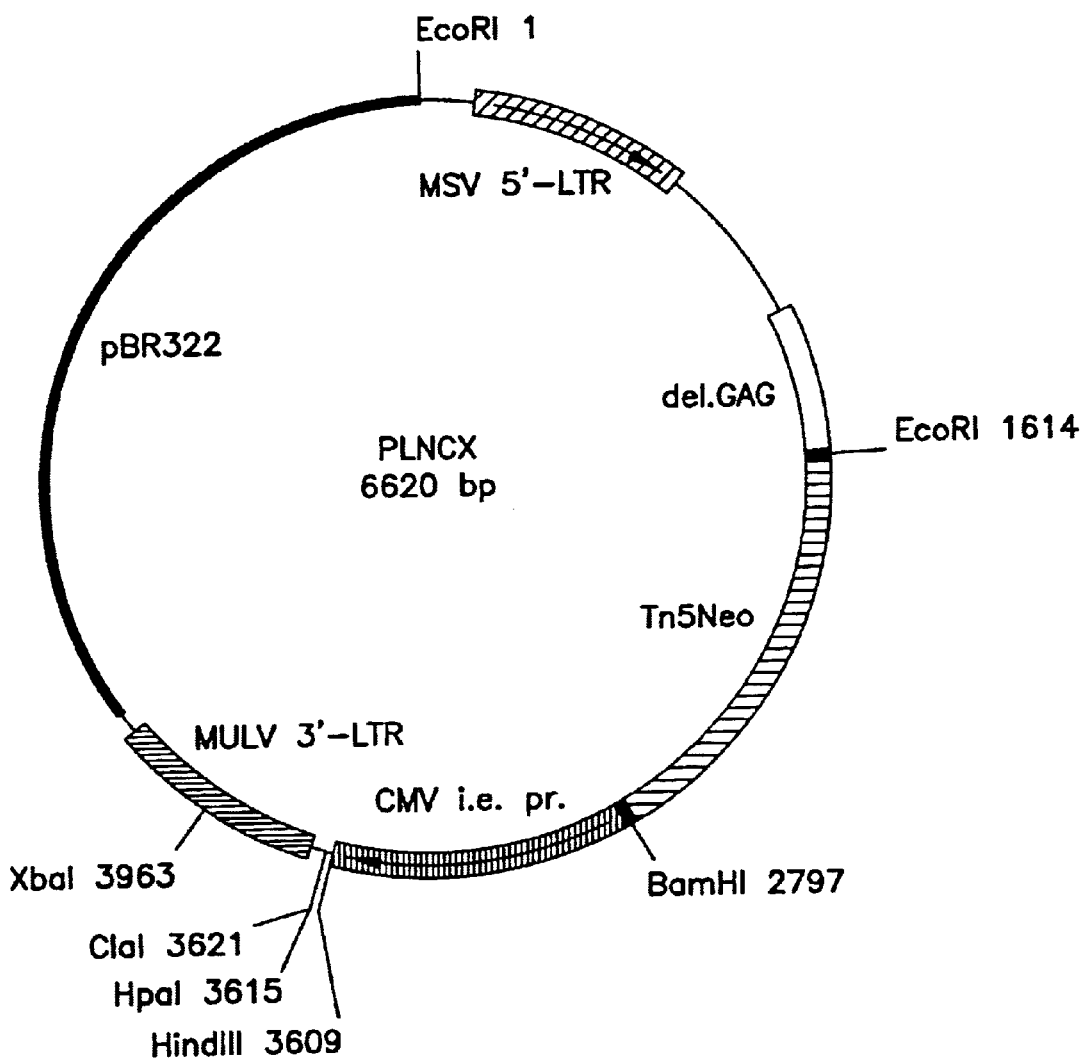
FIG. 6 is diagram of plasmid PLNCX.

Initially three different retroviral vectors were tested for sFv expression levels in transient transfections in Cos cells. Only one vector produced satisfactory expression levels of protein, i.e. pLNCX (FIG. 6) (Miller and Rosman (1989) BioTechniques 7:980–990). A purified Hind-III/Cla-I fragment from clone 2VB7#5 was ligated into the Hind-III/Cla-I cloning sites of pLNCX.

Six clones (pLNC-2VB75#1–6) were tested for expression by transient transfection into Cos cells. At 48 h post transfection, surface expression of the sFv was tested. The cells on microscope slides were fixed in 2% formaldehyde in PBS for 15 min at RT and then washed briefly with PBS. No detergent permeabilization was used. Non-specific epitopes were blocked for 30 min. at RT in 2% BSA, 10% normal goat serum (NGS) in PBS w. Ca and μg. Primary reagent was 8 ml/μg CD28-mIg in 10% NGS, PBS w. Ca and μg for 60 min. at RT. Secondary antibody was goat anti-mouse Ig-FITC at a 1/100 dil. (TAGO, approx. 1 μg/ml in 10% NGS, PBS w. Ca and μg).

Clones #2–6 were positive, while clone #1 was negative as expected (wrong insert). Clone pLNC-2VB75#3 (5NC3) was used for all subsequent studies.

Production of packaging cell lines producing retroviruses transducing the 2e12-hIgG1(Fc-)-hB7-1Tm construct and isolation of expressing clones of the human carcinoma lines Hela, H3347 and 2987. Twenty μg of pLNC-2VB75#3 DNA was transfected on a 10 cm plate of the ecotropic packaging cell line PE501 by calcium phosphate precipitation. After 16 h incubation, the medium was replaced (DME, 10k FBS) and transiently produced retrovirus was recovered in the culture medium after a further 24 h. incubation.

The virus-containing medium (10 ml) was filtered through a 0.2 mm Gelman Acrodisc syringe filter. Hexadimethrine bromide was added to a final 8 μg/ml and the medium was added to a 25–30% confluent 10 cm plate of the primate specific retroviral packaging cell line PG13.

After overnight incubation, the medium was changed and the cells were grown to between 36 and 48 h post infection. At this time, the cells were trypsinized and reseeded in 10 cm plates at different plating densities in DME, 10% FBS, 500 μg/ml (active concentration) of G418. This selective medium was changed with 2 day intervals until colonies of 2–3 mm dia. were visible. These colonies were isolated by scraping off and aspirating in <10 ml with a micropipet.

The isolated cells were trypsinized in 50 ml trypsin solution, which was added to 4 ml of DME, 10% FBS in the well of a six-well plate. When confluent, the cells were again trypsinized and reseeded into one 10 cm dish and one square dish with three microscope slides for immunostaining.

Five PG13 clones were stained for surface expression of the sFv. Clones PG13-NC3#1,#5, #7, #8, #9 were stained as described above but using CD28-hIg-biotin at 10 μg/ml, 60 min, RT, followed by streptavidin-FITC at 5 μg/ml, 30 min, RT. All clones were positive, but clones PG13-NC3#5, #7, #8 showed best expression. All clones were frozen in LN2.

Infection and subcloning of human Hela, H3347 and 2987 carcinoma cells was done using virus-containing medium from Pg13-NC3#5 cells as described above for viral infection of PG13 cells and selection was in DME, 10% FBS, 500 μg/ml G418.

Clones were tested by immunostaining with goat anti-human Ig-FITC and/or CD28hIG-biotin. Hela clones NC3-2, -6, -8, -13 and -15 were frozen. H3347 and 2987 clones were tested before subcloning and were positive for surface expression of 2e12-hIgG1, but subclones Were not tested. Twelve clones of each line were frozen for future testing.

Figure 1B:
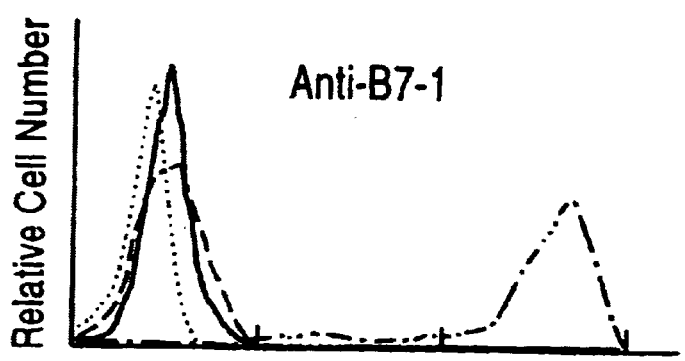
Figure 1C:
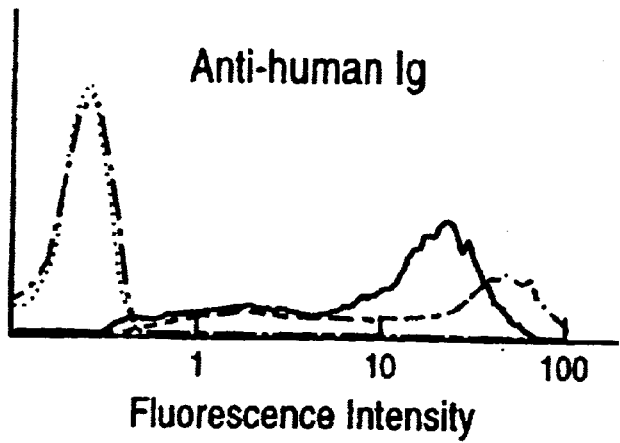

Hela cells infected with retroviral constructs NC3-2 (_____), 58-32 ( - - - - ), B7-1 ( · - · - · - ), or non-infected cells ( . . . . ) (FIG. 1). FIG. 1 shows that Hela cells infected with the 58-32 or NC3-2 retroviruses express the 2E12 sFv on the cell surface as detected either by binding to CD28 or by binding to anti-human Ig. The Hela cells infected with the B7-1 retrovirus express high levels of B7-1.

Figure 2A:
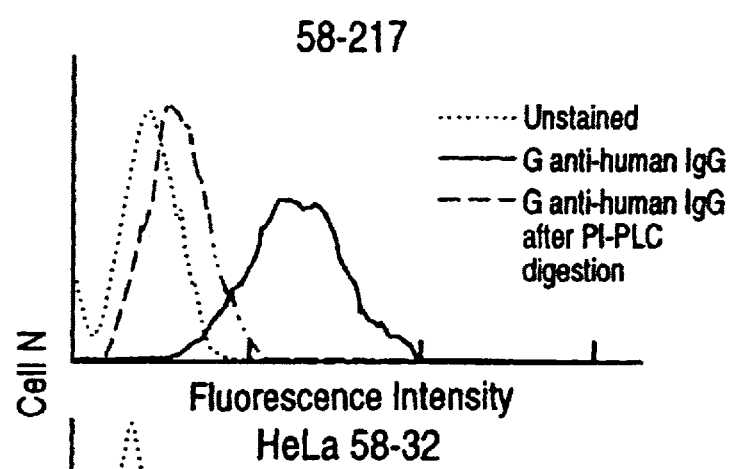
FIG. 2 is a FACS analysis showing that the GPI anchor from CD58 is cleaved by phospholipase C in the NIH3T3 retrovirus packaging cell line, but is resistant to phospholipase C digestion in the 58-32 Hela cell line. NIH3T3 virus packaging cells (A) or Hela cells (B) infected with retroviral constructs containing the 2E12 sFv-Ig fusion protein linked to a CD58 GPI anchored tail. Surface expression of the 2E12 sFv was analyzed by flow cytometry prior to (_____) or following ( - - - ) PI-PLC digestion.
Figure 2B:
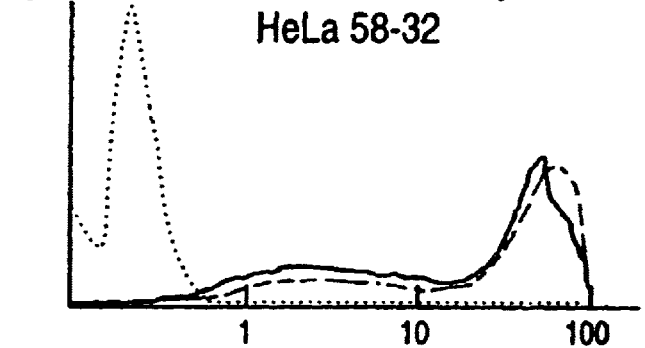

The GPI anchor from CD58 is cleaved by phospholipase C in the NIH3T3 retrovirus packaging cell line, but is resistant to phospholipase C digestion in the 58-32 Hela cell line (FIG. 2). NIH3T3 virus packaging cells (A) or Hela cells (B) infected with retroviral constructs containing the 2E12 sFv-Ig fusion protein linked to a CD58 GPI anchored tail. Surface expression of the 2E12 sFv was analyzed by flow cytometry prior to (_____) or following ( - - - ) PI-PLC digestion.

Figure 3:
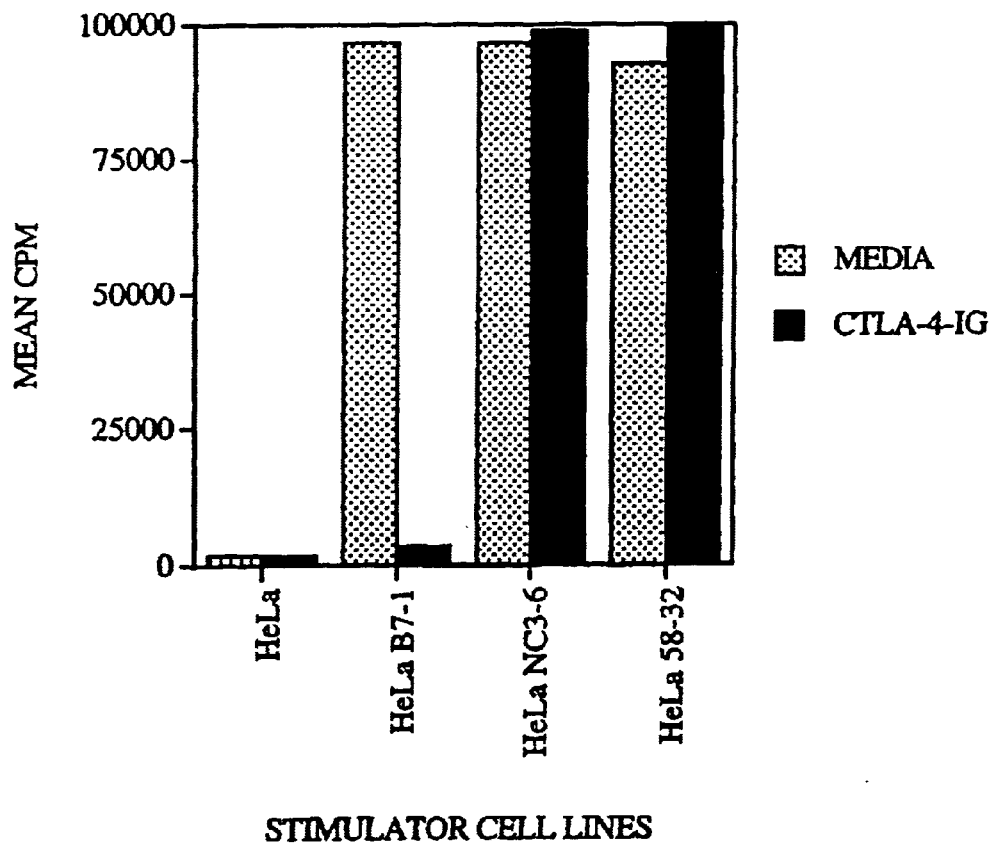
FIG. 3 is a bar graph showing that Hela cells expressing the anti-CD28 sFv are equivalent to the Hela cells expressing B7-1 (CD80) in their ability to stimulate T cell proliferation. The signal to the T cells is specific for the CD28 receptor, and that the activity is not due to a ligand that binds to CTLA-4, such as B7-1 (CD80) or B7-2 (CD86).

FIG. 3 is a bar graph showing stimulation of proliferation of T cell blasts with Hela cells expressing anti-CD28 sFv or B7-1 on the cell surface. Rested day 7 PHA T cell blasts were cocultured for 2 days with irradiated Hela cells or Hela expressing B7-1 or the CD28 sFv at a 1:10 ratio of stimulator cells to T cells, and proliferation was measured by uptake of $^3$H-thymidine for the last 6 hours. Mean proliferation was determined from quadruplicate cultures, and the standard errors were less than 10% of the mean at each point. CTLA4-Ig (2 μg/ml) was added to the cultures as indicated.

This shows that the signal to the T cells is specific for the CD28 receptor, and that the activity is not due to a ligand that binds to CTLA-4, such as B7-1 or B7-2.

Figure 4:
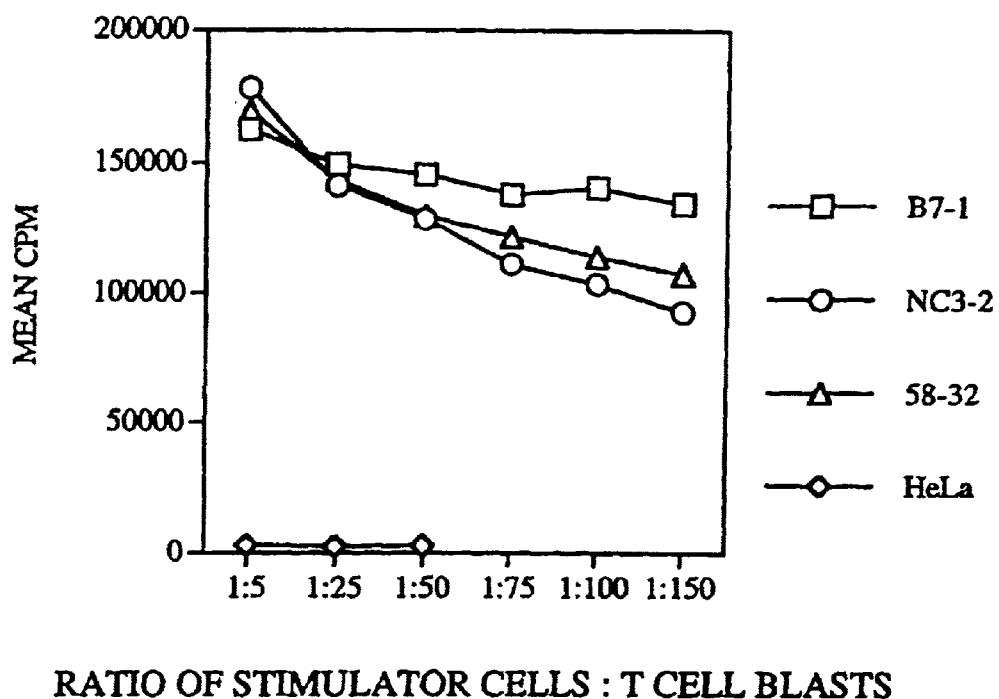
FIG. 4 is a line graph showing titration of Hela stimulator cells for induction of proliferation of rested T cell blasts. Hela NC3-2 and Hela 58-32 cells expressing the 2E12 sFv on the surface were comparable to the Hela B7-1 (CD80) cells for their ability to induce proliferation.

In FIG. 4, T cells were present at a constant 5×10$^4$ cells per well, while the irradiated Hela cell lines were titered as indicated. Proliferation was measured by incorporation of $^3$H-thymidine in quadruplicate cultures of a 96 well microtiter plate, and standard errors did not exceed 10% of the mean at any point.

This shows that the Hela NC3-2 and Hela 58-32 cells expressing the 2E12 sFv on the surface were comparable to the Hela B7-1 cells for their ability to induce proliferation.

Figure 5:
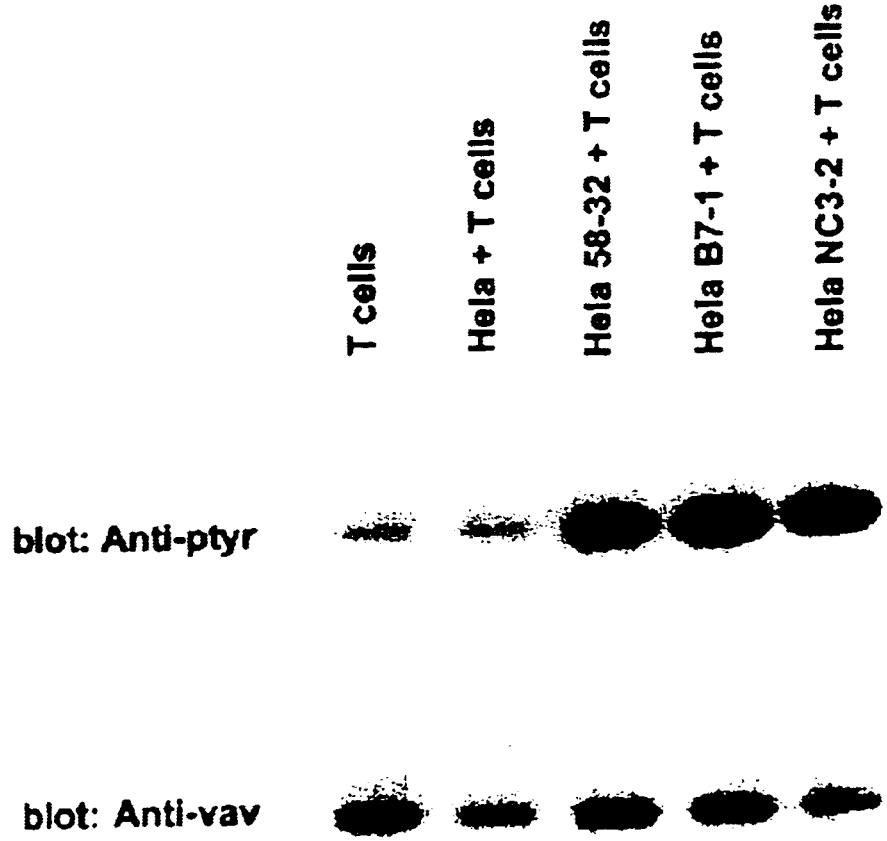
FIG. 5 is a photograph of a gel showing induction of tyrosine phosphorylation of vav protooncogene by Hela cells expressing ligands for human CD28. Hela cells expressing the cell surface 2E12 sFv are equivalent to the Hela cells expressing B7-1 (CD80) for their ability to rapidly activate the tyrosine kinases that phosphorylate the vav protooncogene.

In FIG. 5, cells were pelleted and rapidly lysed in 1% NP40-containing lysis buffer and nuclei were removed by centrifugation. The vav protooncogene was immunoprecipitated from the lysates using 4 μg of polyclonal anti-vav followed by Protein A-Sepharose (Koch et al. (1991) Science 252:668). The immunoprecipitates were extracted in SDS sample buffer and electrophoresed on 10% polyacrylamide gels. The gel was then transferred to a PVDF filter and blotted with rabbit anti-phosphotyrosine Ab followed by detection with $^{125}$I-Protein A and autoradiography. The PVDF filter was then stripped with 2 washes using pH 2.2 glycine-HCl at 70° C. for one hour each. The filter was then blotted again with rabbit anti-vav to determine the amount of vav present in each lane.

FIG. 5 shows that the Hela cells expressing the cell surface 2E12 sFv are equivalent to the Hela cells expressing B7-1 for their ability to rapidly activate the t-yrosine kinases that phosphorylate the vav protooncogene.

EXAMPLE 2

Construction of the retroviral vector pLNC-2e12-hIgG1-hCD58GPI: The sequence of a cDNA for the human GPI (glyco-phosphoinositol) linked form of CD58 (LFA-3) has been reported (Seed, B. 1987, Nature, 329:840–842). From this sequence, bases 631 through 739 were isolated by PCR amplification (FIG. 12F). The fragment encodes aa 207 through 237, i.e. the C-terminal signal sequence and 9 aa of the extracellular domain, including the serine attachment site for the GPI anchor.

Two oligonucleotides were synthesized, covering the bases 631–739 with a 17 base overlap. These were: SCD58GPI, 5'-CTGCATCCTGGAT CCA AGC AGC GGT CAT TCA AGA CAC AGA TAT GCA CTT ATA CCC ATA CCA TTA GCA GTA ATT AC-3' (SEQ ID NO: 15) and ACD58GPI, 5'-CAGCGTTTGCTCGAGATTGTCTTCT-CAA TTA AAG AAC ATT CAT ATA CAG CAC AAT ACA TGT TGT AAT TAC TGC TAA TGG-3' (SEQ ID NO: 16). The bases in bold face indicate the overlapping sequence.

In addition, two PCR primers were used: SCD58BAM, comprising the first 36 bases of SCD58GPI and ACD58XHO, comprising the first 43 bases of ACD58GPI.

The CD58 GPI anchor was amplified using 10 nM each of SCD58GPI and ACD58GPI and 1 mM each of SCD58BAM and ACD58XHO primers with 4 initial cycles at 94 C, 30 sec., 45 C, 30 sec., 72 C, 2 min. and 30 subsequent cycles at 94 C., 30 min., 68 C, 30 sec., 72 C, 2 min. The 137 base pair product was purified and restricted with BamH-I and Xho-I and the resulting 117 bp product was purified over a QIA Quick cartridge and ligated at a 2:1 molar ratio into the BamH-I and Xho-I cleaved pSFVDNA-1-2V7 vector (see above). Briefly, the 50 ml ligation reaction contained 0.07 pmole of the 2V7 vector and 0.15 pmole of the CD58GPI fragment.

Of 18 colonies screened, 16 contained the correct BamH-I/Xho-I fragment. Clones pSFVDNA-1-2e12-hIgG1(Fc-)-CD58GPI#58-2, #58-3, #58-6 were tested (Jun. 21, 1995) for expression in Cos cells, by membrane staining with goat anti-humanIg-FITC, CD28-hIg-Biotin and mAb HP6058 (mouse anti-human IgG1, 2, 3 Fc region).

The Hind-III/Cla-I insert in pSFVDNA-1 clones 58-2, 58-3 and 58-6 were separately cloned into Hind-III/Cla-I cleaved PLNCX vector and one correct clone from each ligation, pLNC2e12-hIgG1-(Fc-)-CD58GPI #58-21, #58-32, #58-64, was further tested by transient expression in Cos cells.

all three clones were positive for membrane staining with goat anti human IgG-FITC and CD28-hIgG-biotin. Cos cells simultaneously transfected with a pLNCX clone of the human B7-1 (CD80, see below) was used as a control.

PG13 packaging cells were generated for the three retroviral clones pLNC-2e12-hIgG (Fc-) CD58GPI #58-21, #58-32, #58-64 as described above. Bulk G418 selected PG13 cells were tested and found positive for membrane staining with goat anti-human IgG-FITC and CD28-hIgG-biotin. Pg13 clones were isolated from #58-32 and #58-64 cells, and were retested for expression as above.

Construction of the pLNC-hB7-1 Retroviral Vector

Figure 9:
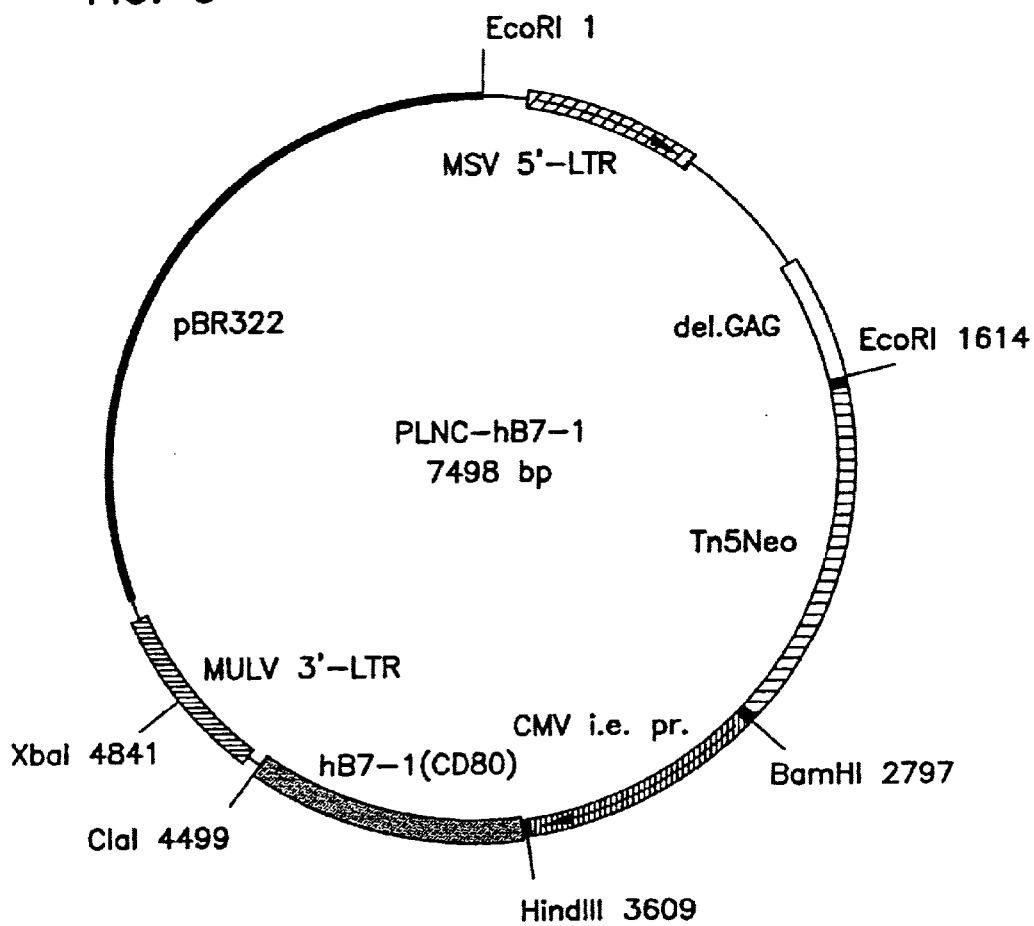
FIG. 9 is a diagram of plasmid PLNC-hB7-1.

A retroviral vector expressing the normal human B7-1 cDNA was constructed as a control for comparative analyses of the functions of the membrane anchored forms of the 2E12 sFv (FIG. 9). This vector is isogenic with the constructs described above, except with regard to the CD28 ligand moiety. A clone of the human B7-1 cDNA in the vector pCDNA-1 was configured for cloning into the Hind-III/Cla-I cleaved PLNCX vector by PCR.

The primers used were SHB71ATG: 5'GTGAATTC-CAAGCTTCCACC ATG GGC CAC ACA CGG AGG CAG-3' (SEQ ID NO: 17) and AHB71TM, described above.

Amplification conditions were 30 cycles at 94 C, 30 sec., 68 C, 1 min., 72 C, 2 min. The 908 bp PCR product was cleaved with Hind-III and Cla-I and the resulting 888 bp cleavage product was gel-purified and ligated into the pLNCX vector. Three clones, pLNC-hB7-1#1, #2, #3 were tested for expression by transfection into Cos cells. All three were positive by staining with anti-B7-1 mAb (B&D, BB-1) followed by goat anti-mouseIg-FITC or with CD28Ig-biotin, followed by streptavidin-FITC.

PG13 packaging cells were generated as described above. These were immunostained after G418 selection as above and were found positive, and clones were isolated and tested. Clone PG13-B7-1#12 (B7-112) showed the strongest surface flourescence. Several clones were frozen.

TABLE 1

T-cell growth stimulation by HeLa cells expressing hB7-1 or membrane-bound 2E12 sFv.

| | $^3$H-Thymidine incorporation[1]. | |
|---|---|---|
| | – blasts | + blasts |
| Presenting cells: | | |
| None | | 16701 (1%) |
| CHO B7-1 | <1000 | 128402 (3%) |
| HeLa | <1000 | 2501 (2%) |
| HeLa B7-1[2] | <1000 | 67246 (1%) |
| HeLa NC3-2[3] | <1000 | 120729 (6%) |
| HeLa NC3-6[3] | <1000 | 118310 (3%) |
| HeLa 58-3[4] | <1000 | 144502 (2%) |
| HeLa 58-6[4] | <1000 | 61422 (<1%) |
| a-CD28 mAb: | | |
| 9.3 mAb | | 58782 (<1%) |
| 9.3 mAb + 187.1 Ab | | 98303 (3%) |

[1]Average of three cultures of 4 × 10$^4$ 7-day PHA blasts + 10$^4$ irradiated target cells incubated 3 days followed by 6 h. pulse w. $^3$H-Thymidine.
[2]HeLa cells inf. with pLNC-hB7-1 virus.
[3]HeLa cells inf. with pLNC-2e12-Ig-B7-1(Tm) virus.
[4]HeLa cells inf. with pLNC-2e12-Ig-CD58GPI virus.

EXAMPLE 3

Materials and Methods

PCR Amplification of Variable Region Genes and Construction of Expression Cassettes: Total cellular RNA from 5×10$^7$ hybridoma cells was isolated using rapid lysis in NP-40 or a modification of the single step acid-guanidinium thiocyanate protocol (Chomczynski P., et al. Single step method of RNA isolation by acid guanidmium thiocyhanade phenol-choroform extraction. Anal Biochem 1987: 162: 156–159.). RNA was reverse transcribed with AMV reverse transcriptase (Life Sciences) and either random primers or antisense oligonucleotides that annealed to specific mouse kappa light chain or heavy chain constant region sequence approximately 100 bases downstream of the J-C junction. Typically, 10 µg RNA and 1 µg primer was used to generate cDNA.

The first strand was then poly-G tailed using terminal transferase (Stratagene), dGTP, and an antisense nested primer that annealed approximately 50 bases from the murine kappa light chain or heavy chain constant region J-C junction. The tailed cDNA was-amplified by PCR as described previously (Gilliand L K, et al. Rapid and reliable cloning of antibody variable regions and generation of recombinant single chain antibody fragments. Tissue Antigens 1996: 47: 1–20).

Anti-L6 mAb is specific for a cloned tumor antigen (Marken J S, et al. Cloning and expression of the tumor associated antigen L6. Proc Natl Acad Sci USA 1992: 89: 3503–3507.) that is expressed at high levels on certain human tumors (Fell H P, et al. Chimeric L6 anti-tumor antibody. Genomic construction, expression, and characterization of the antigen binding site. J Biol Chem 1992: 267: 15552–15558. The sFv for L6 was cloned and expressed as described previously (Hayden M S, et al. Single-chain mono-and bispecific antibody derivatives with novel biological properties and anti-tumor activity from a COS cell transient expression system. Ther Immunol 1994: 1: 3–15.; Fell H P, et al. Chimeric L6 anti-tumor antibody. Genomic construction, expression, and characterization of the antigen binding site. J Biol Chem 1992: 267: 15552–15558).

Secondary PCR was used to add restriction sites for subcloning into the appropriate locations. The bispecific αCD28-αL6 (9.3/L6) sFvIg fusion cassette was constructed by cutting the 9.3 sFvIg at BclI and inserting an L6 sFv as a BclI-BclI fragment directly adjacent to the 3' end of 9.3. The 2e12 mAb is a second mouse anti-human CD28 specific molecule, and the sFv was cloned and expressed as described elsewhere (Gilliand L K, et al. Rapid and reliable cloning of antibody variable regions and generation of recombinant single chain antibody fragments. Tissue Antigens 1996: 47: 1–20).

Plasmid Vectors for Expression of Soluble and Membrane Bound sFv: A modified version of the mammalian expression vector pCDM8 has been described previously (Hayden M S, et al. Single-chain mono-and bispecific antibody derivatives with novel biological properties and anti-tumor activity from a COS cell transient expression system. Ther Immunol 1994: 1: 3–15.). In addition to this vector used for transient expression of sFv fusion proteins, a second vector has been generated for use in generating stable cell lines expressing these fusion proteins.

Briefly, the sFvIg cassettes were subcloned as HindIII-XbaI fragments into the polylinker region adjacent to the CMV promoter in a modified version of pD16, a derivative of pCDNA3 (Invitrogen). The vector contains a DHFR gene with an attenuated promotor and an AscI linearization site in a second polylinker region outside of the expression cassette and DHFR regions. Several restriction sites present in the original pD16 plasmid were removed by PCR mutagenesis to simplify subcloning of -Ig fusion proteins into the pD18 vector.

A modified version of the retroviral expression vector pLNCX was generated as described previously. This vector was then used to construct a 2e12-Ig-B7-1 transmembrane and cytoplasmic tail (TM+CT) fusion cassette for cell surface expression of sFv molecules. The 9.3 sFv region was cut with HindIII and BclI and substituted for the 2e12 HindIII-BglII sFv fragment, creating a second CD28 sFv fusion cassette attached to the huIgG1 and CD80 transmembrane and cytoplasmic tail.

Generation of Tumor Lines Expressing Membrane Bound sFV and CD80: Gene fusion constructs of the sFv or CD80Igs in pLNCX were transfected into PE501 ecotropic packaging cells by CaPO$_4$ precipitation. After 16 hours of incubation, the medium was replaced (DMEM/10% FBS), and transiently produced retrovirus was recovered in the culture medium after a further 24 hour incubation. The virus containing medium (10 ml) was filtered through a 0.2 µm Acrodisc syringe filter (Gelman). Hexadimethrine bromide was added to a final concentration of 8 µg/ml and the medium was added to a 25–30% confluent 10 cm plate of the primate specific retroviral packaging cell line PG13.

After overnight incubation, the medium was changed and the cells were grown for 24–36 hours post infection. At this time, the cells were treated in Versene (PBS) and reseeded 0.2 g/L EDNA-4Na ph 7.0 in 10 cm plates at different plating densities in DMEM/10% FBS. After 24 hours, media was changed to DMEM/10% FBS/500 µg/ml G418.

The media was changed in 2-day intervals until colonies of 2–3 mm diameter were visible. The colonies were isolated by scraping and aspirating in <10 µl using a micropipeter. The isolated colonies were trypsinized in 100 µl versene solution, which was then added to 4 ml DMEM/10% FBS/500 µg/ml G418 in a single well of a 6 well cluster plate.

When confluent, the cells were again Versene and reseeded into one 10 cm dish. Individual clones of cells were isolated and stained for 2e12 or 9.3 sFvIg surface expression. Two clones for 9.3 (designated #4-1 and #6-4), and one each for 2e12 (designated 3-2/3c) and CD80 (designated B7-112) were selected for further use because of higher expression levels of the molecules on the cell surface.

H3347 tumor cells expressing high levels of the L6 antigen were transfected with retroviral vectors containing membrane bound versions of the 9.3 (designated 9.3 4-1 b1 and 9.3 6-4 a4) and 2e12 (designated 3-2/3c) anti-CD28 sFvIg. Similar stable lines were generated which expressed human CD80 (designated B7-112).

Infection and subcloning of H3347 tumor cells was done using virus containing media from these PG13 clones. H3347 clones were all positive for 9.3 sFvIg surface expression by staining with biotinylated-CD28Ig (B-CD28Ig) followed by streptavidin-phycoerythrin (SA-PE); or FITC-anti human IgG.

Cell Culture, Transfection, and Purification of Soluble sFvIg Molecules: The hybridoma producing murine anti-human CD28 (9.3) was used. Additionally, the anti-L6 human tumor specific hybridoma and 2e12 anti-hCD28 hybridoma were used.

COS cells were transfected with sFvIg expression plasmids isolated from 3–6 clones of MC1061/p3 transformants as previously described (Hayden M S, et al. Single-chain mono-and bispecific antibody derivatives with novel biological properties and anti-tumor activity from a COS cell transient expression system. Ther Immunol 1994: 1: 3–15; Gilliand L K, et al. Rapid and reliable cloning of antibody variable regions and generation of recombinant single chain antibody fragments. Tissue Antigens 1996: 47: 1–20). Three days following transfection, culture supernatants were collected and tested for the presence of sFv-Ig fusion protein, and for specific binding activity of the protein.

Positive clones from this initial screening were then selected and large scale transfections performed. Usually 500–1000 ml of serum free supernatant was collected over a nine day culture period. Protein was isolated and purified from culture supernatants as described previously (Hayden M S, et al. Single-chain mono-and bispecific antibody derivatives with novel biological properties and anti-tumor activity from a COS cell transient expression system. Ther Immunol 1994: 1: 3–15; Gilliand L K, et al. Rapid and reliable cloning of antibody variable regions and generation of recombinant single chain antibody fragments. Tissue Antigens 1996: 47: 1–20).

Stable CHO lines were generated by high copy electroporation of CHO DG44 cells (Barsoum J. Introduction of stable high-copy-number DNA into Chinese hamster ovary cells by electroporation. DNA Cell Biol 1990: 9: 293–300; Urlaub G, et al. Effect of gamma rays at the dihydrofolate reductase locus: deletions and inversions. Somat Cell Mol Genet 1986: 12: 555–566.) with linearized pD18 expression plasmid containing the sFvIg expression cassettes. Approximately 250 μg plasmid DNA was digested with AscI, phenol/chloroform extracted, and coprecipitated with 200 μg sheared herring sperm DNA as carrier.

Transfections were performed by mixing 1×10$^7$ CHO DG44 cells (Urlaub G, et al. Effect of gamma rays at the dihydrofolate reductase locus: deletions and inversions. Somat Cell Mol Genet 1986: 12: 555–566) with DNA in 0.8 ml PFCHO (JRH Biosciences) containing 4 μg/ml hypoxanthine, 0.72 μg/ml thymidine, 4 mM glutamine, and 0.5 μg/ml recombulin insulin in an electroporation cuvette (Biorad) and electroporating at 300 volts, 960 μF. Cells were transferred to T25 flasks and incubated in 10 ml non-selective media for 1–2 days prior to plating in selective media containing 100 nM methotrexate.

Transfected clones were ready to screen by ELISA within 2–3 weeks of plating. ELISAs were performed as described previously (Gilliand L K, et al. Rapid and reliable cloning of antibody variable regions and generation of recombinant single chain antibody fragments. Tissue Antigens 1996: 47: 1–20), with serial dilutions from a 1:100 starting solution of culture supernatant. Clones expressing higher levels of the fusion proteins were amplified for 7–12 days in 6% $CO_2$ gassed spinner flasks containing selective media. Cultures were filtered through Gelman suporcap-50 or -100 0.2 μm filters into roller bottles using a Cole-Parmer Masterflex pump and pump drive prior to protein A purification.

SDS PAGE and Western Blotting: SDS PAGE and Western Blotting were performed as described previously (Hayden M S, et al. Single-chain mono-and bispecific antibody derivatives with novel biological properties and anti-tumor activity from a COS cell transient expression system. Ther Immunol 1994: 1: 3–15; Gilliand L K, et al. Rapid and reliable cloning of antibody variable regions and generation of recombinant single chain antibody fragments. Tissue Antigens 1996: 47: 1–20).

Immunostaining and FACS analysis: Binding of antibodies and fusion proteins to Jurkat T cells, CD28CHO cells, L6 positive tumor cells, transfected tumor cells, or purified T lymphocytes was analyzed by indirect immunofluorescence. Single cell suspensions were obtained by treating monolayer cultures with a solution of EDTA (0.2 g/L) dissolved in PBS.

Cells were incubated with antibodies or fusion proteins at the indicated concentrations in staining media (RPMI 1640+ 5% FBS+0.1% sodium azide) for 1 hour on ice. Cells were washed and bound proteins detected with goat anti-mouse IgG or anti-human IgG conjugated to FITC (Biosource International) for 40 minutes on ice.

Some assays were performed by a three step incubation involving the anti-CD28 fusion protein first followed by biotinylated CD28Ig or αL6Ig, and then PE conjugated streptavidin (PE-SA). Other assays with sFv transfected tumor cells involved incubation in biotinylated CD28Ig, L6, or αCD80, followed by PE-SA. Cells were washed with ice-cold staining media and fixed in PBS containing 0.2% paraformaldehyde prior to fluorescence analysis using a FACSCAN cell sorter (Becton Dickinson and Co.). Usually 10,000 cells were analyzed per sample.

Proliferation Assays: Lymphocytes were isolated from peripheral blood of healthy human volunteers using Lymphoprep Separation Media (Organon Teknika). PHA activated T cell blasts were prepared by culturing PBL with 1 μg/ml PHA (Wellcome) for 6 days, and resting 1 day in media lacking PHA. L6-positive tumor cells (H2981, H3347, and CD28- or CD80-transfected H3347 cells) were exposed to 5,000 rads prior to use in proliferation assays.

Lymphocytes were cultured in round-bottom 96-well tissue culture plates (Costar) at 5×10$^4$ cells/well in RPMI 1640 medium containing 10% FBS in a final volume of 0.2 ml. Fusion proteins were tested as purified protein at the concentrations indicated. Fusion proteins were either added in solution to PBL, or where indicated, were prebound to the tumor cells with soluble protein removed by washing before incubating with PBL. Proliferation was measured in triplicate samples by uptake of [$^3$H] thymidine at 1 μCi/ml added during the last 6 hours of a three day culture.

Cloning and sequencing 9.3 variable region genes: The 9.3 hybridoma produces antibody specific for human CD28 expressed on T cells (Jung G, et al. Induction of cytoxicity in resting human T lymphocytes bond to tumor cells by antibody heteroconjugates. Proc Natl Acad Sci USA 1987: 84: 4611–4615). The isotype of the antibody is mouse IgG2a with k light chain, so the primers used for the first strand synthesis step were either random primers or the specific primers for heavy and light chain constant regions mIgG2a-1 (VH) with the sequence 5'CAGGTCAAGGTCACTGGCTCAGG-3' (SEQ ID NO:18), and mIgck-1 (VL) with the sequence 5'CTTCCACTTGACATTGATGTCTTTG-3' (SEQ ID NO: 19) (Ollo R, et al. Comparison of mouse immunoglobulin gamma2a and gamma2b chain genes suggests that exons can be exchanged between genes in a multigenic family. Proc Natl Acad Sci USA 1981: 78: 2442–2446). The VH and VL cDNA were poly-G tailed and were then amplified by PCR using the ANCTAIL 5' primer 5'CGTCGATGAGCTCTA-GAATTCGCAT GTGCAAGTCCGATGGTCCC-CCCCCCCCCCC-3' (SEQ ID NO: 20) (Gilliand L K, et al. Rapid and reliable cloning of antibody variable regions and generation of recombinant single chain antibody fragments. Tissue Antigens 1996: 47: 1–20) and the nested 3' primers HBS-mG2a ($V_H$) 5'CGTCATGTCGACGGATCCC-AAGCTTGAGCCAGTTGTATCTCCACACACAG-3' (SEQ ID NO: 21) (24) and HBS-mck ($V_L$) 5'-CGTCATGTCTGACGGATCCA AGCTTCAA-GAAGCACACGA-CTGAGGCAC-3' (SEQ ID NO: 22) (Altenburger W, et al. DNA sequence of the constant gene region of the mouse immunoglobulin kappa chain. Nucleic Acids Res 1981: 9: 971–981).

A single DNA band of approximately 500 bp was observed after agarose gel electrophoresis of aliquots from each PCR reaction, representing leader, V gene, and about 50 bases encoding the constant region. PCR products were then restriction digested with Hind III and XbaI and purified fragments subcloned into PUC19, amplified in DH5α, and plasmid DNA prepared to screen for inserts. Subclones containing 500 bp inserts were then subjected to DNA sequence analysis and 3–4 clones used to determine consensus sequence for the variable regions.

Subclones with correct sequence were then used as templates in PCR reactions that attached the appropriate sequences to fragments for assembly of an sFv. Rather than performing SEWING PCR, a Bam HI restriction site was introduced at the 3' end of the (gly$_4$ser)$_3$ linker, and the entire linker sequence was attached to the 3' end of $V_L$ by PCR, using a 78-mer oligonucleotide with the following sequence: 5'CTGGGCCTGGGATCCACCGCCGCCT GAACCGC-CACCTCCAGAACCGCCACCACCCGAAGC-CCGTTTTATTTCCAGCTT3' (SEQ ID NO: 23). The native leader for the 9.3 $V_L$ was used for assembly of the sFv and a HindIII site was attached by PCR using the following 36-mer oligonucleotide as primer: 5'GGACTGCT-GAAGCTTATG GAGTCAGACACACTCCTG3' (SEQ ID NO: 24).

PCR products were then digested with HindIII and BamHI, and subcloned into pUC19. BamHI and BclI sites were attached to the 5' and 3' ends of the $V_H$ domain using the 36-mer sense primer 5'CTGGGACTGGGATCCCTG-GCTCAGGT GCAGCTGAAG-3' (SEQ ID NO: 25) and the 39-mer antisense primer 5'GGTGGAGGTTGATCAGAGG AGACGGTGACTGAGGTTCCT3' (SEQ ID NO: 26).

The PCR product from the $V_H$ domain was subcloned into a pUC19 vector containing L6 sFvIg which had been digested with BamHI and BclI. The 9.3 $V_H$Ig vector was then digested with HindIII and BamHI and ligated to the HindIII+BamHI ($V_L$-linker) cassette. DNA from these transformants was then digested with HindIII and XbaI to screen for a full length sFvIg fragment. The HindIII-XbaI fragments with the appropriate size for a full length sFvIg were transferred to the expression vector pCDM8 and DNA prepared for transfection of COS cells. The nucleotide and deduced amino acid sequence for the 9.3 sFv, including the $V_L$-leader, $V_L$, linker, and $V_H$, is shown in FIG. 13.

Production, Expression, and Screening of 9.3 sFvIg and 9.3/L6 sFvIg Fusion Proteins: COS cell supernatants were screened for the presence of 9.3 sFvIg fusion protein by IgG sandwich ELISA and by immunoprecipitation with protein-A, SDS-PAGE, and Western blotting to visualize precipitated proteins. Using these two screening assays, two out of three clones were shown to express protein reactive with anti-human Ig reagents. Upon sequencing, the clone that was negative for protein expression was found to contain a Tyr to Cys mutation in the CDR3 region of the heavy chain variable region, indicating that a PCR induced mutation accounted for the lack of expression.

The 9.3/L6 bispecific fusion cassette was created by fusing the αCD28 and αL6 $V_L V_H$ cassettes directly to one another without any intervening linker sequence following directly after the JH4 region of 9.3. The bispecific expression cassette was inserted into the pCDM8 expression vector at the same location as the monospecific sFvIg constructs. Each of the L6 sFvIg, 9.3 sFvIg, and 9.3/L6 sFvIg gene fusions were transfected into COS cells and crude culture supernatants assayed for the presence of protein as described above.

FIG. 14 shows the results of Western Blot analysis on the 9.3 sFvIg, L6 sFvIg, mock transfected, and 9.3/L6 sFvIg transfection supernatants. COS cell supernatants were immunoprecipitated with Staphylococcus protein A, washed, and subjected to SDS-PAGE. Gels were blotted to nitrocellulose and incubated with alkaline-phophatase conjugated goat anti-human IgG to visualize proteins. SFvIg proteins for L6 (Lane 4) and 9.3 (Lane 2) migrate at $M_r$ 55,000, the approximate. size expected for these fusion proteins. Supernatants from mock transfected cells (Lane 1) show no protein, while supernatants from the 9.3/L6 sFvIg bispecific (Lane 3) migrate at $M_r$ 83,000, the approximate size expected for the bispecific protein.

Binding activity of the 9.3 and 9.3/L6 sFvIg Fusion Protein: The binding of each sFvIg fusion protein was assayed by immunostaining and FACS analysis. The bispecific 9.3/L6 sFvIg, 9.3 sFvIg and L6 sFvIg molecules at 1 µg/ml were incubated with H2981 L6 positive tumor cells to assay binding to the L6 molecule as shown in FIG. 15A. The 9.3 sFvIg and the negative control including only second step were identical and are shown in the Figure as control. 9.3 sFvIg and 9.3/L6 sFvIg were incubated with CD28 CHO cells and binding was detected using FITC anti-human IgG as shown in FIG. 15B. Purified CD28+ T cells were incubated with (1) FITC labeled anti-L6 idiotype 13B, (2) the bispecific 9.3/L6 sFvIg followed by FITC 13B, or (3) preblocked with 9.3 sFvIg, then bound to 9.3/L6 sFvIg and FITC 13B as shown in panel 15C. The results of these assays demonstrate functional binding activity for both the 9.3 sFvIg and the 9.3/L6 sFvIg. Staining with either the mono- or bispecific fusion proteins plus second step was similar to staining with native 9.3 antibody. Staining for the L6 portion of the bispecific fusion protein was reduced when compared to native L6 antibody or the L6 sFvIg monospecific construct so that the binding observed at equivalent concentrations was comparable to that of the L6 antibody at half the concentration (1 µg/ml looks like 0.5 µg/ml native antibody), indicating that the binding activity of the second sFv (L6) in this particular fusion protein was less than that of the first sFv (9.3). The reduced level of binding may be due to the absence of a linker region between the sFvs in this bispecific molecule.

Comparison of Costimulation by soluble 9.3 sFvIg and soluble CD80Ig: To determine if soluble 9.3 sFvIg was equivalent to CD80Ig at providing costimulatory signals to T cells, 7-day resting PHA blasts were co-cultured for three days with equal concentrations of the sFvIg or CD80Ig molecule with and without anti-human IgG or protein A as crosslinking reagents.

Figure 19:
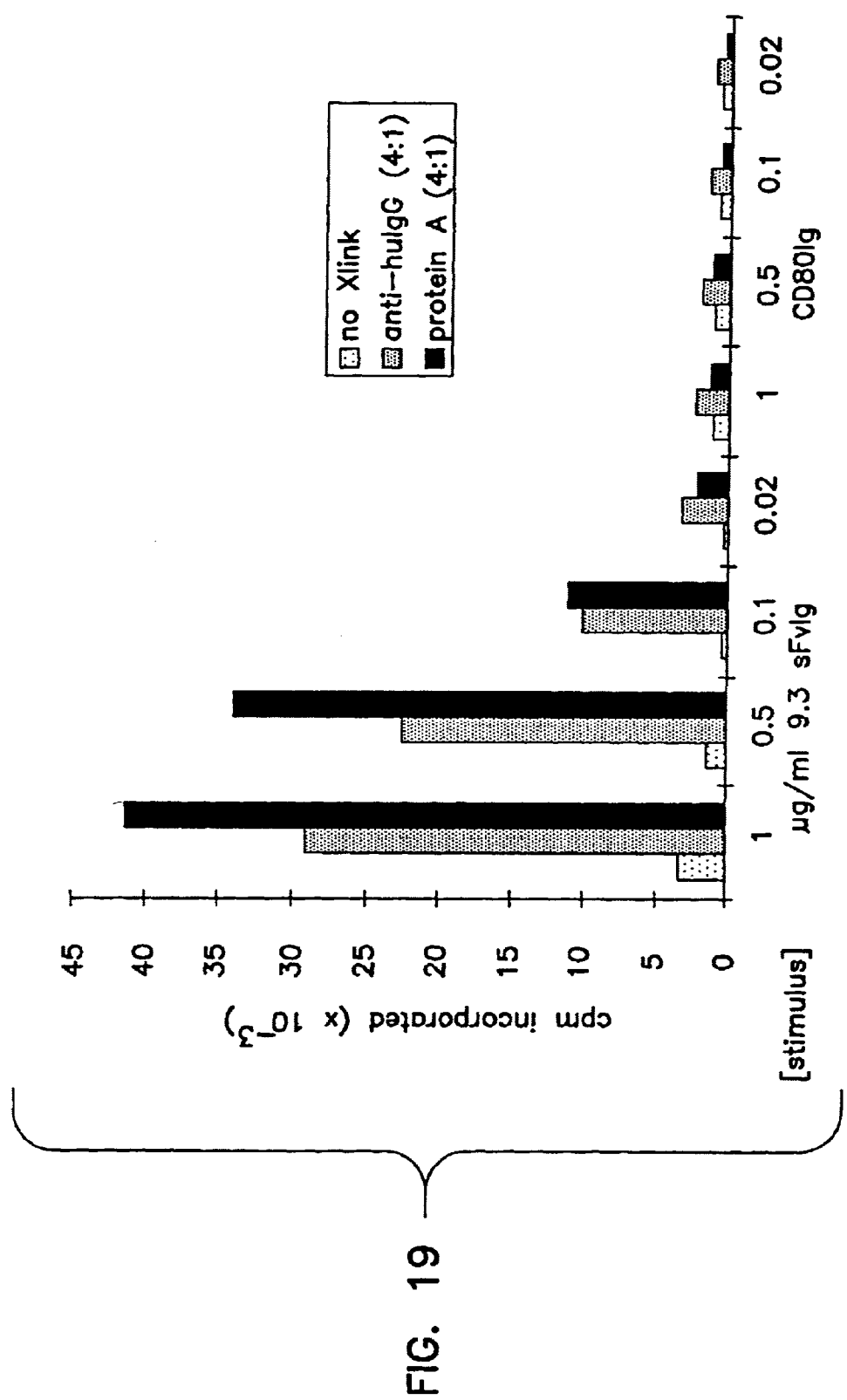
FIG. 19 is a bar graph showing a comparison of costimulation by soluble 9.3 sFvIg and soluble CD80Ig. 7-day resting PHA blasts were cocultured for 3 days with dilutions (20 ng/ml, 0.1 μg/ml, 0.5 μg/ml, and 1 μg/ml) of the 9.3 sFvIg or CD80Ig. Stimuli were incubated with no crosslinker anti-human IgG 4:1 (protein:IgG), or protein A at 4:1 (protein:protein A. [$^3$H]-thymidine incorporation was measured during the last six hours of the assay. Results are displayed as (cpm incorporated×10$^{-3}$). All data are the mean of triplicate samples. SEM is 6% or less.

[$^3$H]-thymidine incorporation was measured during the last 6 hours of the assay. 9.3 sFvIg and CD80Ig molecules were present in soluble form at 0.02 µg/ml, 0.1 µg/ml, 0.5 µg/ml, or 1.0 µg/ml. Stimuli were incubated with no crosslinking, anti-human IgG at 4:1 (protein: IgG), or protein A at 4:1 (protein: protein A). The results of this experiment are shown in FIG. 19. The CD80Ig molecule alone generates little or no costimulatory signal without crosslinking, although crosslinking enhances the signal somewhat at higher concentrations. In contrast the 9.3 sFvIg is able to generate stronger costimulatory signals than CD80Ig under identical conditions. Crosslinking greatly enhances costimulation generated by the 9.3 sFvIg. Although the magnitude of costimulation fluctuated from experiment to experiment and from donor to donor, more significant responses were obtained using 9.3 sFvIg than the CD80Ig at every concentration tested and for every experimental treatment. Similarly, crosslinking enhanced costimulation by 9.3 sFvIg more significantly than by CD80Ig. In some experiments, CD80Ig was found to suppress costimulation rather than enhancing it.

Figure 16:
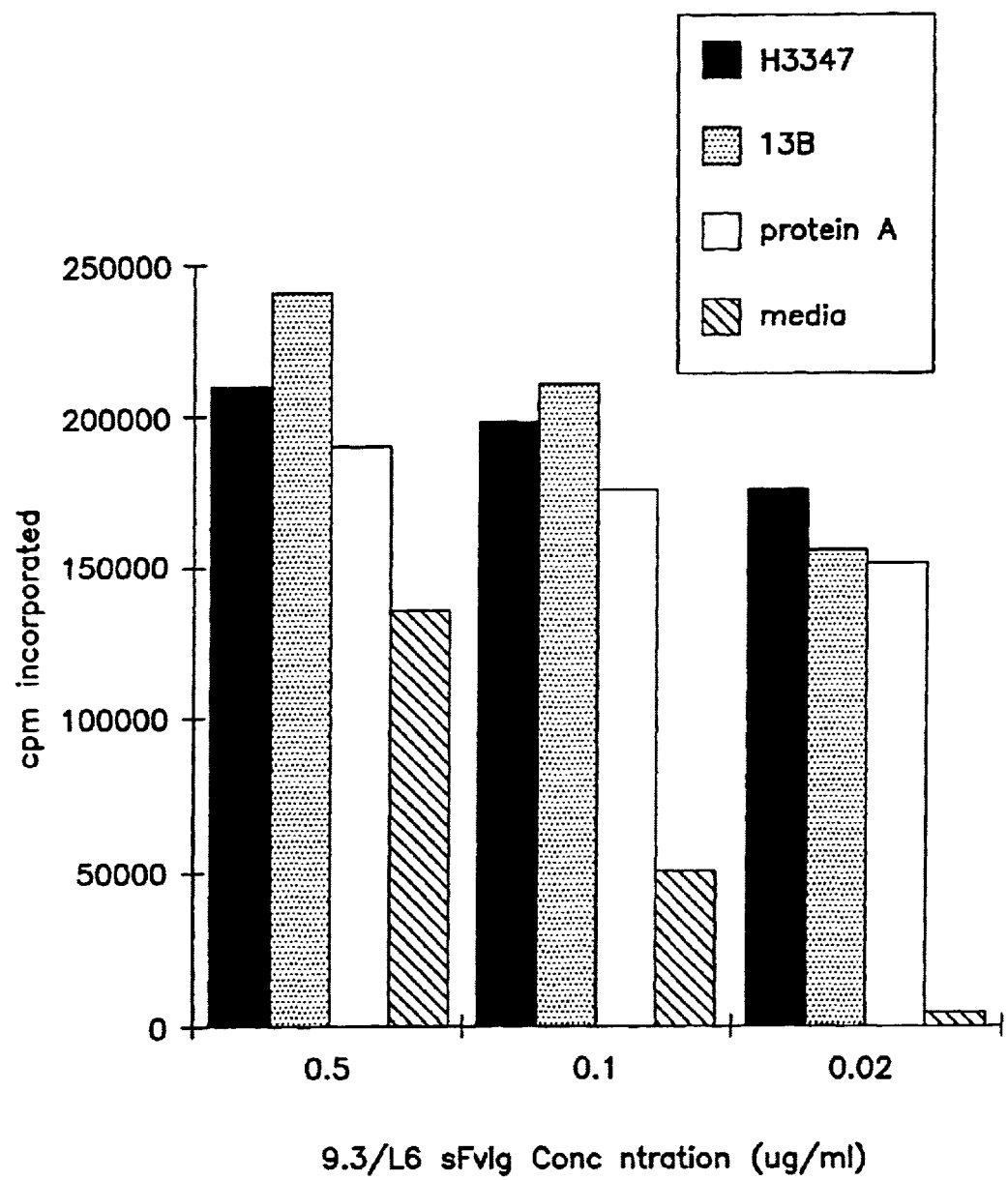
FIG. 16 is a bar graph showing 9.3/L6 sFvIg mitogenicity in resting CD28+ PHA blasts.

Titration of 9.3/L6 sFvIg mitogenicity in resting PHA blasts: The ability of the bispecific 9.3/L6 sFvIg fusion protein to provide costimulatory signals to T cells and the levels of protein required to observe costimulatory effects were examined. Rested PHA blasts were incubated with dilutions of bispecific 9.3/L6 sFvIg fusion protein at concentrations of 0.5 µg/ml, 0.1 µg/ml, and 0.02 µg/ml. As shown in FIG. 16, higher concentrations of bispecific protein (0.5 µg/ml) gave proliferation without addition of other reagents, although the mitogenic effects of the molecule were augmented by the presence of crosslinking reagents or L6 positive tumor cells. However, at lower concentrations of bispecific 9.3/L6 sFvIg, crosslinking of the molecule by protein A, anti-L6 idiotype 13B, or H3347 tumor cells was required to generate a significant proliferative response.

In FIG. 16, seven day PHA blasts ($5 \times 10^4$ cells/well) were incubated with dilutions of bispecific 9.3/L6 sFvIg fusion protein at concentrations of 0.5, 0.1 and 0.02 µg/ml. At each dilution, the sFvIg and blasts were coincubated with 0.5 µg/ml protein A, α-L6 idiotype 13B (2 µg/ml), H3347 tumor cells, or no other reagent. H3347 cells were irradiated at 5,000 rads, preincubated with sFvIg, washed, and incubated at a 1:5 E:T cell ratio in the indicated samples. All data are obtained from triplicate samples for each treatment, and SEM are <6%.

These results show that at high concentrations, greater than 0.1 µg/ml, bispecific 9.3/L6 sFvIg alone can induce proliferation of T cell blasts. This activity is not dependent on binding of the L6 variable region of the bispecific, but occurs by CD28 mediated activation signals only, a pattern of costimulation that may be undesirable for tumor targeting. At these high concentrations, a significant increase in proliferative responses results from coincubation with L6 positive tumor cells or crosslinking reagents. However, 0.02 µg/ml of fusion protein requires the presence of tumor cells or crosslinking to produce significant proliferation, so we chose to explore costimulation under these conditions in more detail.

Figure 17:
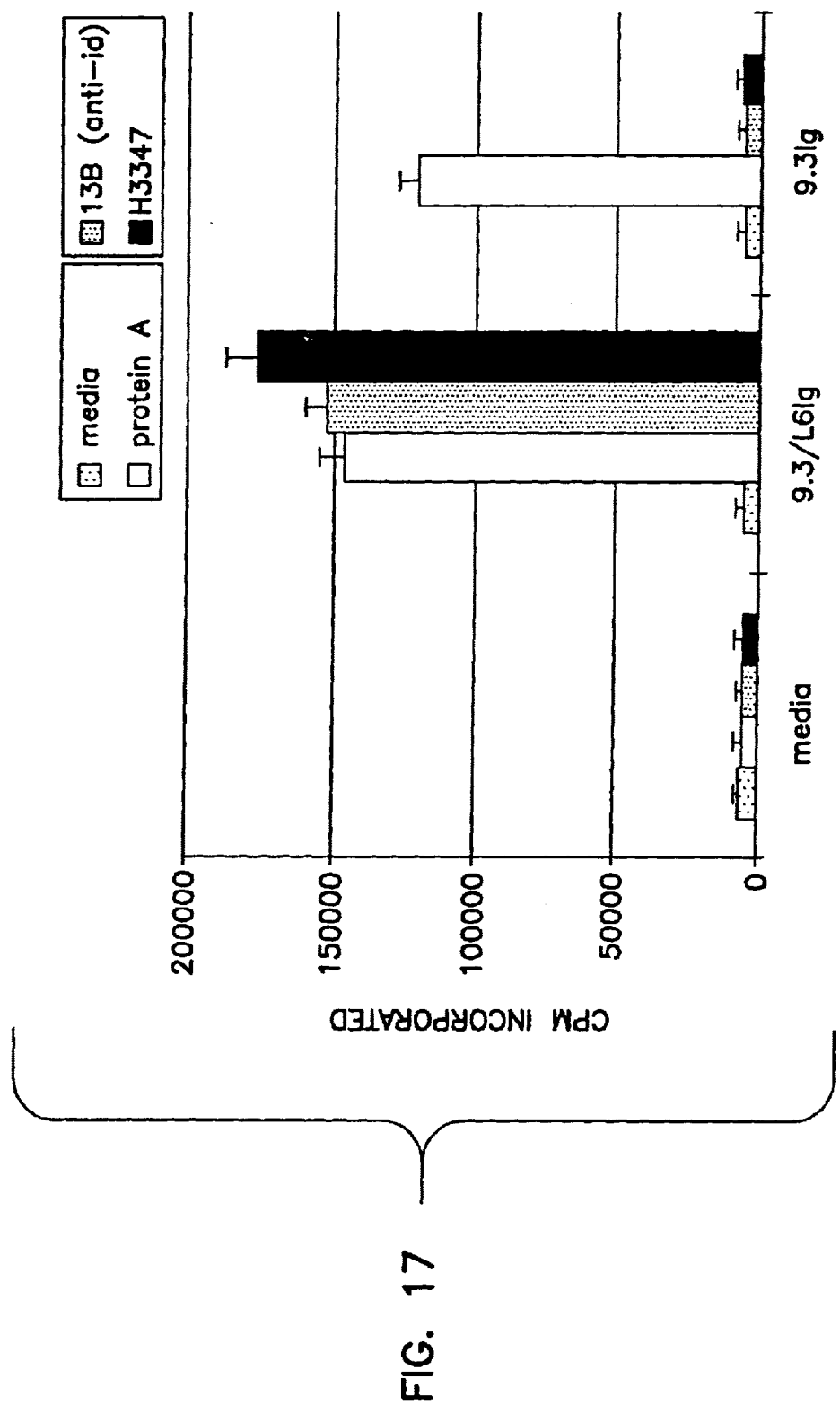
FIG. 17 is a bar graph comparing the abilities of 9.3/L6 sFvIg and 9.3 sFvIg molecules to stimulate T cell proliferation in the presence of tumor cells or crosslinking reagents.
Figure 18:
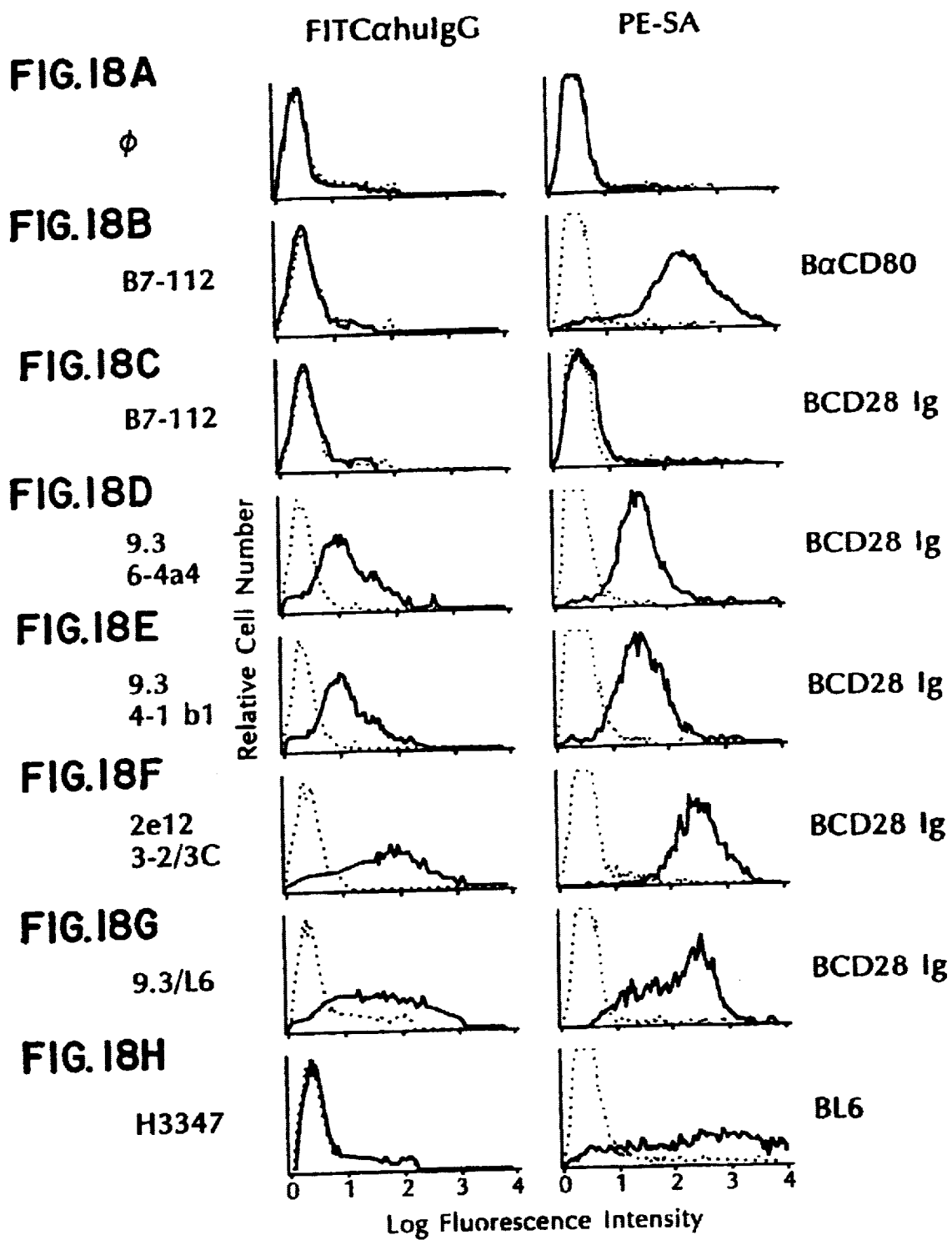
FIGS. 18A–18H are line graphs showing expression of CD28 or CD80 on transduced H3347 experimental tumor lines. H3347 tumor cell transfectants were assessed for cell surface expression of the sFvIg or B7 molecules by indirect immunofluorescence using 1:100 FITC anti-human IgG, B-CD28Ig and PE-streptavidin for 9.3 transfectants and 9.3/L6 sFvIg, B-L6 and PE-streptavidin for staining H3347 cells, or B-αCD80Ig plus PE streptavidin for B7 transfectants. Cells were washed, resuspended in staining media, and analyzed by flow cytometry. A total of 10,000 cells was analyzed for each sample. Transduced cell clones are each identified on the left side of the figure. The first panel of curves shows the fluorescence profile obtained using FITC anti-human IgG on transduced clones with (_____) and without ( - - - - - ) FITC label, and the second panel shows staining with the PE-streptavidin conjugate for each transfected clone or sFvIg bound cell, PE-SA alone ( - - - - - ) and B-molecule indicated plus PE-SA (_____). The biotin-labeled reagent used on each clone is identified on the right side of the second panel.

Comparison of the abilities of 9.3/L6 sFvIg and 9.3 sFvIg molecules to stimulate T cell proliferation in the presence of tumor cells or crosslinking reagents: The conditions necessary to produce T cell proliferation dependent upon both the CD28 and L6 binding activities of the bispecific protein were determined. FIG. 17 shows the results of an assay where resting PHA blasts were incubated with low concentrations (20 ng/ml) of bispecific 9.3/L6, 9.3 sFvIg fusion protein, or media, where crosslinking of surface bound CD28 and costimulation does not occur in the presence of these stimuli alone.

In FIG. 17, seven day resting PHA blasts ($5 \times 10^4$ cells/well) were incubated with either monospecific or bispecific fusion protein at 20 ng/ml, a concentration where CD28 receptor binding alone fails to result in costimulation. The molecules were crosslinked through their Fc domain with protein A at 0.5 µg/ml, through the L6 epitope with L6 anti-idiotype 13B at 2 µg/ml, or by actively binding L6 antigen on the surface of H3347 tumor cells. H3347 tumor cells were irradiated, preincubated with sFvIg, washed, and incubated at a 1:5 E:T cell ratio in the indicated wells. The results demonstrate that the bispecific molecule but not the 9.3 sFvIg can be crosslinked by coincubation with H3347 tumor cells and PHA blasts, generating a powerful mitogenic signal for T cell proliferation.

Monospecific 9.3 sFvIg was mitogenic for T cell proliferation when crosslinked using protein A but failed to stimulate proliferation when incubated with media, mAb 13B, or irradiated H3347 tumor cells. Only bispecific 9.3/L6 sFvIg was mitogenic in the presence of 13B or tumor cell crosslinking, demonstrating that the costimulatory activity of the 9.3/L6 sFvIg at low concentrations was dependent either on engagement of both sFvs or on some less tumor specific method of achieving crosslinking. Because crosslinking of surface bound CD28 is required for costimulatory signals, engaging both of the binding sites of the bispecific molecule must be sufficient to crosslink the CD28 receptor and trigger T cell activation.

For successful tumor targeting, stimulation should be limited to those instances where the costimulatory molecule has actually bound to its tumor antigen target and not occur from an antigen-independent engagement of the CD28 receptor alone. The data above demonstrate that at low concentrations, costimulation requires crosslinking of the bispecific molecule to stimulate proliferation, and that binding to both the T cell surface and tumor antigen is sufficient to crosslink the CD28 receptor on the T cell surface.

Generation of H3347 experimental tumor lines expressing membrane bound CD80 and 9.3 sFv: The costimulatory activity generated by bispecific sFv coated tumor cells was compared to that generated by tumor cell surface expression of sFv.

H3347 tumor cells were transfected with the pLNCX retroviral expression vector containing CD80-anchored 2e12 sFvIg, CD80-anchored 9.3 sFvIg, or the native CD80 molecule. Transfectants were assessed or cell surface expression of the sFvIg or CD80 molecule by indirect immunofluorescence using FITC anti-human IgG (all samples), biotinylated CD28Ig (B-CD28Ig) and PE-streptavidin (9.3 transfecants and 9.3/L6 sFvIg), B-L6 and PE-streptavidin (H3347 cells) or B-aCD80Ig plus PE-streptavidin (for CD80 transfectants) followed by flow cytometry analysis.

The results shown in FIGS. 18a–g demonstrate the specificity of staining using these reagents for both transfected tumors and 9.3/L6 sFvIg bound tumors. Those transfectants expressing the CD28 sFvs gave positive signals for binding to both CD28Ig and FITC anti-human IgG.

The CD80 expressing tumors were negative for binding FITC anti-human IgG and B-CD28Ig/PE-streptavidin yet positive for binding to the B-αCD80/PE-streptavidin combination. The CD28Ig-B7 binding interaction is apparently too weak to detect with the B-CD28Ig, so that only B7 specific antibody was positive for binding. The expression level of sFv or B7 varies from clone to clone, with the lowest level expressed by 9.3 clone 6-4, followed by 9.3 clone 4-1, B7-112, and 2e12 clone 3-2/3c. The shift in fluorescence indicating amount of 9.3/L6 sFvIg binding to H3347 cells was less than the shift observed for cell surface expression of 2e12 and CD80, but greater than the shift observed for the 9.3 clones.

Comparison of costimulatory activities of transfected H3347 tumor cells and 9.3/L6 sFvIg coated tumor cells: The bispecific sFvIg molecule and cell surface expression of the CD28 sFv on tumor cells were compared as methods of providing costimulatory signals to T cells. Rested 7 day PHA blasts were cocultured for three days with irradiated transfected H3347 tumor cells expressing CD80, the 2e12 sFv, the 9.3 sFv, or no exogenous fusion protein. In addition, dilutions of the 9.3/L6 sFvIg bispecific were cocultured with PHA blasts alone or with PHA blasts and untransfected tumor cells. The results of this experiment, shown in Table 2, demonstrate similar levels of T cell proliferation generated by cell surface expressed CD80, 2e12, or 9.3.

A proliferative response was also observed using the bispecific fusion protein alone at high concentrations (nonantigen specific stimulation), or at low concentrations so long as tumor cells were also present (antigen specific targeting of stimulation). These results indicate that the bispecific molecule can function as a costimulatory molecule at a level comparable to that of cell surface expressed sFv or native ligand. This has important implications for the soluble molecule approach to tumor immunotherapy as an alternative to ex vivo culture and gene therapy. The results also indicate that the CD28 specific sFvs may be more efficient at costimulation than the CD80 molecule at equivalent cell densities, and that cell surface expression of sFvs may be another promising approach for stimulating tumor specific immune responses.

The data shows that expression of the ligands for CD28 and CTLA-4 by tumor cells enhances their immunogenicity and promotes both CD4$^+$ and CD8$^+$ T cell mediated tumor rejection under the appropriate conditions (Chen L, et al. Tumor immunogenicity determines the effect of B7 costimulation on T cell-mediated tumor immunity. J Exp Med 1994: 179: 523–532; Chen L, et al. Costimulation of antitumor immunity by the B7 counter-receptor for the T lymphocyte molecules CD28 and CTLA-4. Cell 1992: 71: 1093–1102; Ramarathinam K, et al. T cell costimulation by B7/BB1 induces CD8 T cell-dependent tumor rejection: an important role of B7/BB1 in the induction, recruitment, and effector function of antitumor T cells. J Exp Med 1994: 179: 1205–1214; Johnston J V, et al. B7-CD28 costimulation unveils the hierarchy of tumor epitopes recognized by major histocompatibility complex class I-restricted CD8+ cytolytic T lymphocytes. J Exp Med 1996: 183: 791–800; Baskar S, et al. Constitutive expression of B7 restores immunogenicity of tumor cells expressing truncated major histocompatibility complex class II molecules. Proc Natl Acad Sci USA 1993: 90: 5687–5690; Levitsky H I, et al. Immunization with granulocyte-macrophage colony-stimulating factor-transduced, but not B7-1-transduced, lymphoma cells primes idiotype-specific T cells and generates potent systemic antitumor immunity. J Immunol 1996: 156: 3858–3865). Artificial adhesion receptors were constructed on the cell surface using the 9.3 and 2e12 sFvIgs fused to the CD80 cytoplasmic and transmembrane domains. The data demonstrates that transfection of the cell surface forms of the two different CD28 sFvIgs into H3347 human tumor cells causes them to generate significant costimulatory signals to resting T cell blasts in vitro. The data also demonstrates costimulation using untransfected tumor cells coated with a single chain bispecific αCD28-αL6 sFvIg fusion protein.

This approach to triggering tumor specific immune responses resulted in similar levels of T cell proliferation in vitro.

TABLE 2

Comparison of costimulatory activities of transfected tumor lines with 9.3/L6 SFvIg coated cells.

| H3347 Clone | 1:5 | 1:25 | 1:100 |
| --- | --- | --- | --- |
| 9.3 4-1 b1 | 102 | 37 | 11.7 |
| 9.3 6-4 a4 | 95.3 | 35.3 | 8.8 |

TABLE 2-continued

Comparison of costimulatory activities of transfected tumor lines with 9.3/L6 SFvIg coated cells.

| B7-112 | 65.4 | 26.4 | 5.2 |
| --- | --- | --- | --- |
| 2e12 3-2/3c | 117 | 73.6 | 28 |

| 9.3/L6 | +H3347 | no H3347 cells |
| --- | --- | --- |
| 0.5 µg/ml | 144.7 | 69.2 |
| 0.1 µg/ml | 115 | 9.6 |
| 0.05 µg/ml | 97.8 | 4 |

| H3347 untransfected | cells washed 3x |
| --- | --- |
| 9.3/L6, 1 µg/ml | 98 |
| media | 2.6 |
| Blasts alone | 1.4 |
| H3347 alone | 1.9 |

In Table 2, rested 7-day PHA blasts were cocultured for three days with irradiated transfected H3347 tumor cells expressing CD80 (B7-112), the 2e12 sFv (2e12 3-2/3c), the 9.3 sFv (9.3 4-1b1 or 9.3 6-4 a4), or untransfected cells, at E:T ratios of 1:5, 1:25, or 1:100. Alternatively, the 9.3/L6 sFvIg bispecific was incubated in solution at 0.5 µg/ml, 0.1 µg/ml and 0.05 µg/ml with PHA blasts or with blasts and tumor cells (untransfected) at an E:T ratio of 1:5. The bispecific protein was also preincubated with untransfected tumor cells at 1 µg/ml, washed once or three times, and cocultured with the PHA blasts at an E:T ratio of 1:5. Cultures were pulsed during the last 6 hours of the three day assay with [$^3$H]-thymidine. Results are tabulated as cpm incorporated×10$^3$. Each total is the mean of triplicate samples, and SEM f 6% for all data.

SEQUENCE LISTING (1) GENERAL INFORMATION:

(iii) NUMBER OF SEQUENCES: 39

(2) INFORMATION FOR SEQ ID NO:1:

(i) SEQUENCE CHARACTERISTICS:
      (A) LENGTH: 11 amino acids
      (B) TYPE: amino acid
      (C) STRANDEDNESS: double
      (D) TOPOLOGY: linear (ii) MOLECULE TYPE: peptide (v) FRAGMENT TYPE: internal (xi) SEQUENCE DESCRIPTION: SEQ ID NO:1:

Ala Ala Asn Asp Glu Asn Tyr Ala Leu Ala Ala
1               5                   10

(2) INFORMATION FOR SEQ ID NO:2:

(i) SEQUENCE CHARACTERISTICS:
      (A) LENGTH: 8 amino acids
      (B) TYPE: amino acid
      (C) STRANDEDNESS: double
      (D) TOPOLOGY: linear (ii) MOLECULE TYPE: peptide (v) FRAGMENT TYPE: internal (xi) SEQUENCE DESCRIPTION: SEQ ID NO:2:

Asp Tyr Lys Asp Asp Asp Asp Lys
1               5

(2) INFORMATION FOR SEQ ID NO:3:

(i) SEQUENCE CHARACTERISTICS:
        (A) LENGTH: 4 amino acids
        (B) TYPE: amino acid
        (C) STRANDEDNESS: double
        (D) TOPOLOGY: linear (ii) MOLECULE TYPE: peptide (v) FRAGMENT TYPE: internal (xi) SEQUENCE DESCRIPTION: SEQ ID NO:3:

Ala Leu Ala Leu
1

(2) INFORMATION FOR SEQ ID NO:4:

(i) SEQUENCE CHARACTERISTICS:
        (A) LENGTH: 13 amino acids
        (B) TYPE: amino acid
        (C) STRANDEDNESS: double
        (D) TOPOLOGY: linear (ii) MOLECULE TYPE: peptide (v) FRAGMENT TYPE: internal (xi) SEQUENCE DESCRIPTION: SEQ ID NO:4:

Tyr Pro Tyr Asp Val Pro Asp Tyr Ala Ile Glu Gly Arg
1               5                   10

(2) INFORMATION FOR SEQ ID NO:5:

(i) SEQUENCE CHARACTERISTICS:
        (A) LENGTH: 12 amino acids
        (B) TYPE: amino acid
        (C) STRANDEDNESS: double
        (D) TOPOLOGY: linear (xi) SEQUENCE DESCRIPTION: SEQ ID NO:5:

Lys Gly Phe Ser Tyr Phe Gly Glu Asp Leu Met Pro
1               5                   10

(2) INFORMATION FOR SEQ ID NO:6:

(i) SEQUENCE CHARACTERISTICS:
        (A) LENGTH: 9 amino acids
        (B) TYPE: amino acid
        (C) STRANDEDNESS: double
        (D) TOPOLOGY: linear (ii) MOLECULE TYPE: peptide (v) FRAGMENT TYPE: internal (xi) SEQUENCE DESCRIPTION: SEQ ID NO:6:

Tyr Pro Tyr Asp Val Pro Asp Tyr Ala
1               5

(2) INFORMATION FOR SEQ ID NO:7:

(i) SEQUENCE CHARACTERISTICS:
            (A) LENGTH: 41 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:7:

GTGAATTCCA AGCTTCCACC ATGGATTTTC AAGTGCAGAT T                     41

(2) INFORMATION FOR SEQ ID NO:8:

(i) SEQUENCE CHARACTERISTICS:
            (A) LENGTH: 25 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:8:

AGTGCAGATC TGAGGAGACG GTGAC                                       25

(2) INFORMATION FOR SEQ ID NO:9:

(i) SEQUENCE CHARACTERISTICS:
            (A) LENGTH: 39 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:9:

CTGCATCCGG ATCCGCTTTA CCCGGAGACA GGGAGAGGC                        39

(2) INFORMATION FOR SEQ ID NO:10:

(i) SEQUENCE CHARACTERISTICS:
            (A) LENGTH: 83 base pairs
            (B) TYPE: nucleic acid
            (C) STRANDEDNESS: double
            (D) TOPOLOGY: linear (ii) MOLECULE TYPE: cDNA (xi) SEQUENCE DESCRIPTION: SEQ ID NO:10:

AAGCTGAATT CCAAGCTTGC ATCAGATCTC TCATCTAGAG GTTCGGATCC TTCGAACCGC    60

AGTCTCGAGC ATCGATAGCT AGA                                           83

(2) INFORMATION FOR SEQ ID NO:11:

(i) SEQUENCE CHARACTERISTICS:
            (A) LENGTH: 23 amino acids
            (B) TYPE: amino acid
            (C) STRANDEDNESS: double
            (D) TOPOLOGY: linear (ii) MOLECULE TYPE: peptide (v) FRAGMENT TYPE: internal (xi) SEQUENCE DESCRIPTION: SEQ ID NO:11:

Asn Ser Lys Leu Ala Ser Asp Leu Ser Ser Arg Gly Ser Asp Pro Ser
 1               5                  10                  15

Asn Arg Ser Leu Glu His Arg
            20

(2) INFORMATION FOR SEQ ID NO:12:

(i) SEQUENCE CHARACTERISTICS:
        (A) LENGTH: 10 amino acids
        (B) TYPE: amino acid
        (C) STRANDEDNESS: double
        (D) TOPOLOGY: linear (ii) MOLECULE TYPE: peptide (v) FRAGMENT TYPE: C-terminal (xi) SEQUENCE DESCRIPTION: SEQ ID NO:12:

```
Asp Pro Ser Asn Arg Ser Leu Glu His Arg
 1               5                   10
```

(2) INFORMATION FOR SEQ ID NO:13:

(i) SEQUENCE CHARACTERISTICS:
        (A) LENGTH: 35 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:13:

```
CTGCATCCGT TCGAACCTGC TCCCATCCTG GGCCA                          35
```

(2) INFORMATION FOR SEQ ID NO:14:

(i) SEQUENCE CHARACTERISTICS:
        (A) LENGTH: 47 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:14:

```
CAGCGTTGAC TCGAGTATCG ATTTATACAG GGCGTACACT TTCCCTT             47
```

(2) INFORMATION FOR SEQ ID NO:15:

(i) SEQUENCE CHARACTERISTICS:
        (A) LENGTH: 75 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:15:

```
CTGCATCCTG GATCCAAGCA GCGGTCATTC AAGACACAGA TATGCACTTA TACCCATACC    60

ATTAGCAGTA ATTAC                                                    75
```

(2) INFORMATION FOR SEQ ID NO:16:

(i) SEQUENCE CHARACTERISTICS:
        (A) LENGTH: 79 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:16:

```
CAGCGTTTGC TCGAGATTGT CTTCTCAATT AAAGAACATT CATATACAGC ACAATACATG    60

TTGTAATTAC TGCTAATGG                                                 79
```

(2) INFORMATION FOR SEQ ID NO:17:

(i) SEQUENCE CHARACTERISTICS:
        (A) LENGTH: 41 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:17:

```
GTGAATTCCA AGCTTCCACC ATGGGCCACA CACGGAGGCA G                        41
```

(2) INFORMATION FOR SEQ ID NO:18:

(i) SEQUENCE CHARACTERISTICS:
        (A) LENGTH: 23 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:18:

```
CAGGTCAAGG TCACTGGCTC AGG                                            23
```

(2) INFORMATION FOR SEQ ID NO:19:

(i) SEQUENCE CHARACTERISTICS:
        (A) LENGTH: 25 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:19:

```
CTTCCACTTG ACATTGATGT CTTTG                                          25
```

(2) INFORMATION FOR SEQ ID NO:20:

(i) SEQUENCE CHARACTERISTICS:
        (A) LENGTH: 55 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:20:

```
CGTCGATGAG CTCTAGAATT CGCATGTGCA AGTCCGATGG TCCCCCCCCC CCCCC         55
```

(2) INFORMATION FOR SEQ ID NO:21:

(i) SEQUENCE CHARACTERISTICS:
        (A) LENGTH: 50 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:21:

```
CGTCATGTCG ACGGATCCCA AGCTTGAGCC AGTTGTATCT CCACACACAG               50
```

(2) INFORMATION FOR SEQ ID NO:22:

(i) SEQUENCE CHARACTERISTICS:
        (A) LENGTH: 48 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:22:

```
CGTCATGTCT GACGGATCCA AGCTTCAAGA AGCACACGAC TGAGGCAC              48
```

(2) INFORMATION FOR SEQ ID NO:23:

(i) SEQUENCE CHARACTERISTICS:
        (A) LENGTH: 78 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:23:

```
CTGGGCCTGG GATCCACCGC CGCCTGAACC GCCACCTCCA GAACCGCCAC CACCCGAAGC   60

CCGTTTTATT TCCAGCTT                                                78
```

(2) INFORMATION FOR SEQ ID NO:24:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:24:

```
GGACTGCTGA AGCTTATGGA GTCAGACACA CTCCTG                           36
```

(2) INFORMATION FOR SEQ ID NO:25:

(i) SEQUENCE CHARACTERISTICS:
        (A) LENGTH: 36 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:25:

```
CTGGGACTGG GATCCCTGGC TCAGGTGCAG CTGAAG                           36
```

(2) INFORMATION FOR SEQ ID NO:26:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:26:

```
GGTGGAGGTT GATCAGAGGA GACGGTGACT GAGGTTCCT                        39
```

(2) INFORMATION FOR SEQ ID NO:27:

(i) SEQUENCE CHARACTERISTICS:
    (A) LENGTH: 12 base pairs
    (B) TYPE: nucleic acid
    (C) STRANDEDNESS: double
    (D) TOPOLOGY: linear (ii) MOLECULE TYPE: cDNA (xi) SEQUENCE DESCRIPTION: SEQ ID NO:27:

GGATCCTTCG AA                                                              12

(2) INFORMATION FOR SEQ ID NO:28:

(i) SEQUENCE CHARACTERISTICS:
        (A) LENGTH: 13 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:28:

CTCGAGCATC GAT                                                             13

(2) INFORMATION FOR SEQ ID NO:29:

(i) SEQUENCE CHARACTERISTICS:
        (A) LENGTH: 1527 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:29:

ATTGTGCTCA CCCAATCTCC AGCTTCTTTG GCTGTGTCTC TAGGTCAGAG AGCCACCATC    60

TCCTGCAGAG CCAGTGAAAG TGTTGAATAT TATGTCACAA GTTTAATGCA GTGGTACCAA   120

CAGAAACCAG GACAGCCACC CAAACTCCTC ATCTCTGCTG CATCCAACGT AGAATCTGGG   180

GTCCCTGCCA GGTTTAGTGG CAGTGGGTCT GGGACAGACT TCAGCCTCAA CATCCATCCT   240

GTGGAGGAGG ATGATATTGC AATGTATTTC TGTCAGCAAA GTAGGAAGGT TCCTTGGACG   300

TTCGGTGGAG GCACCAAGCT GGAAATCAAA CGGGGTGGCG GTGGCTCGGG CGGTGGTGGG   360

TCGGGTGGCG GCGGATCTCA GGTGCAGCTG AAGGAGTCAG GACCTGGCCT GGTGGCGCCC   420

TCACAGAGCC TGTCCATCAC ATGCACCGTC TCAGGGTTCT CATTAACCGG CTATGGTGTA   480

AACTGGGTTC GCCAGCCTCC AGGAAAGGGT CTGGAGTGGC TGGGAATGAT ATGGGGTGAT   540

GGAAGCACAG ACTATAATTC AGCTCTCAAA TCCAGACTGA GCATCACCAA GGACAACTCC   600

AAGAGCCAAG TTTTCTTAAA AATGAACAGT CTGCAAACTG ATGACACAGC CAGATACTAC   660

TGTGCCAGAG ATGGTTATAG TAACTTTCAT TACTATGTTA TGGACTACTG GGGTCAAGGA   720

ACCTCAGTCA CCGTCTCCTC TGATCCGGAG CCCAAATCTT GTGACAAAAC TCACACATGC   780

CCACCGTGCC CAGCACCTGA ATTCGAGGGT GCACCGTCAG TCTTCCTCTT CCCCCCAAAA   840

CCCAAGGACA ACCTCATGAT CTCCCGGACC CCTGAGGTCA CATGCGTGGT GGTGGACGTG   900

AGCCACGAAG ACCCTGAGGT CAAGTTCAAC TGGTACGTGG ACGCCGTGGA GGTGCATAAT   960

GCCAAGACAA AGCCGCGGGA GGAGCAGTAC AACAGCACGT ACCGGGTGGT CAGCGTCCTC  1020

ACCGTCCTGC ACCAGGACTG GCTGAATGGC AAGGAGTACA AGTGCAAGGT CTCCAACAAA  1080

GCCCTCCCAG CCCCCATCGA GAAAACCATC TCCAAAGCCA AGGGCAGCCC CGAGAACCA   1140

```
CAGGTGTACA CCCTGCCCCC ATCCCGGGAT GAGCTGAACA AGAACCAGGT CAGCCTGACC    1200

TGCCTGGTCA AAGGCTTCTA TCCCAGCGAC ATCGCCGTGG AGTGGGAGAG CAATGGGCAG    1260

CCGGAGAACA ACTACAAGAC CACGCCTCCC GTGCTGGACT CCGACGGCTC CTTCTTCCTC    1320

TACAGCAAGC TCACCGTGGA CAAGAGCAGG TGGCAGCAGG GGAACGTCTT CTCATGCTCC    1380

GTGATGCATG AGGCTCTGCA CAACCACTAC ACGCAGAAGA GCCTCTCCCT GTCTCCGGGT    1440

AAAAACCTGC TCCCATCCTG GCCATTACC  TTAATCTCAG TAAATGGAAT TTTTGTCATA    1500

TGCTGCCTGA CCTACTGGTT TGCCCCA                                       1527

(2) INFORMATION FOR SEQ ID NO:30:

(i) SEQUENCE CHARACTERISTICS:
        (A) LENGTH: 1509 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:30:

ATTGTGCTCA CCCAATCTCC AGCTTCTTTG GCTGTGTCTC TAGGTCAGAG AGCCACCATC      60

TCCTGCAGAG CCAGTGAAAG TGTTGAATAT TATGTCACAA GTTTAATGCA GTGGTACCAA    120

CAGAAACCAG GACAGCCACC CAAACTCCTC ATCTCTGCTG CATCCAACGT AGAATCTGGG    180

GTCCCTGCCA GGTTTAGTGG CAGTGGGTCT GGGACAGACT TCAGCCTCAA CATCCATCCT    240

GTGGAGGAGG ATGATATTGC AATGTATTTC TGTCAGCAAA GTAGGAAGGT TCCTTGGACG    300

TTCGGTGGAG GCACCAAGCT GGAAATCAAA CGGGGTGGCG GTGGCTCGGG CGGTGGTGGG    360

TCGGGTGGCG GCGGATCTCA GGTGCAGCTG AAGGAGTCAG GACCTGGCCT GGTGGCGCCC    420

TCACAGAGCC TGTCCATCAC ATGCACCGTC TCAGGGTTCT CATTAACCGG CTATGGTGTA    480

AACTGGGTTC GCCAGCCTCC AGGAAAGGGT CTGGAGTGGC TGGGAATGAT ATGGGGTGAT    540

GGAAGCACAG ACTATAATTC AGCTCTCAAA TCCAGACTGA GCATCACCAA GGACAACTCC    600

AAGAGCCAAG TTTTCTTAAA AATGAACAGT CTGCAAACTG ATGACACAGC CAGATACTAC    660

TGTGCCAGAG ATGGTTATAG TAACTTTCAT TACTATGTTA TGGACTACTG GGGTCAAGGA    720

ACCTCAGTCA CCGTCTCCTC TGATCCGGAG CCCAAATCTT GTGACAAAAC TCACACATGC    780

CCACCGTGCC CAGCACCTGA ATTCGAGGGT GCACCGTCAG TCTTCCTCTT CCCCCCAAAA    840

CCCAAGGACA ACCTCATGAT CTCCCGGACC CCTGAGGTCA CATGCGTGGT GGTGGACGTG    900

AGCCACGAAG ACCCTGAGGT CAAGTTCAAC TGGTACGTGG ACGCCGTGGA GGTGCATAAT    960

GCCAAGACAA AGCCGCGGGA GGAGCAGTAC AACAGCACGT ACCGGGTGGT CAGCGTCCTC   1020

ACCGTCCTGC ACCAGGACTG GCTGAATGGC AAGGAGTACA AGTGCAAGGT CTCCAACAAA   1080

GCCCTCCCAG CCCCCATCGA GAAAACCATC TCCAAAGCCA AAGGGCAGCC CCGAGAACCA   1140

CAGGTGTACA CCCTGCCCCC ATCCCGGGAT GAGCTGACCA AGAACCAGGT CAGCCTGACC   1200

TGCCTGGTCA AAGGCTTCTA TCCCAGCGAC ATCGCCGTGG AGTGGGAGAG CAATGGGCAG   1260

CCGGAGAACA ACTACAAGAC CACGCCTCCC GTGCTGGACT CCGACGGCTC CTTCTTCCTC   1320

TACAGCAAGC TCACCGTGGA CAAGAGCAGG TGGCAGCAGG GGAACGTCTT CTCATGCTCC   1380

GTGATGCATG AGGCTCTGCA CAACCACTAC ACGCAGAAGA GCCTCTCCCT GTCTCCGGGT   1440

AAATATGCAC TTATACCCAT ACCATTAGCA GTAATTACAA CATGTATTGT GCTGTATATG   1500

AATGTTCTT                                                          1509
```

(2) INFORMATION FOR SEQ ID NO:31:

(i) SEQUENCE CHARACTERISTICS:
        (A) LENGTH: 752 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:31:

```
GTCGACATTG TGCTCACCCA ATCTCCAGCT TCTTTGGCTG TGTCTCTAGG TCAGAGAGCC    60

ACCATCTCCT GCAGAGCCAG TGAAAGTGTT GAATATTATG TCACAAGTTT AATGCAGTGG   120

TACCAACAGA AACCAGGACA GCCACCCAAA CTCCTCATCT CTGCTGCATC CAACGTAGAA   180

TCTGGGGTCC CTGCCAGGTT TAGTGGCAGT GGGTCTGGGA CAGACTTCAG CCTCAACATC   240

CATCCTGTGG AGGAGGATGA TATTGCAATG TATTTCTGTC AGCAAAGTAG AAGGTTCCT    300

TGGACGTTCG GTGGAGGCAC CAAGCTGGAA ATCAAACGGG GTGGCGGTGG CTCGGGCGGT   360

GGTGGGTCGG GTGGCGGCGG ATCTCAGGTG CAGCTGAAGG AGTCAGGACC TGGCCTGGTG   420

GCGCCCTCAC AGAGCCTGTC CATCACATGC ACCGTCTCAG GGTTCTCATT AACCGGCTAT   480

GGTGTAAACT GGGTTCGCCA GCCTCCAGGA AAGGGTCTGG AGTGGCTGGG AATGATATGG   540

GGTGATGGAA GCACAGACTA TAATTCAGCT CTCAAATCCA GACTGAGCAT CACCAAGGAC   600

AACTCCAAGA GCCAAGTTTT CTTAAAAATG AACAGTCTGC AAACTGATGA CACAGCCAGA   660

TACTACTGTG CCAGAGATGG TTATAGTAAC TTTCATTACT ATGTTATGGA CTACTGGGGT   720

CAAGGAACCT CAGTCACCGT CTCCTCTGAT CA                                 752
```

(2) INFORMATION FOR SEQ ID NO:32:

(i) SEQUENCE CHARACTERISTICS:
        (A) LENGTH: 767 base pairs
        (B) TYPE: nucleic acid
        (C) STRANDEDNESS: double
        (D) TOPOLOGY: linear (ii) MOLECULE TYPE: Other (ix) FEATURE:

(xi) SEQUENCE DESCRIPTION: SEQ ID NO:32:

```
GGATCCGGAG CCCAAATCTT GTGACAAAAC TCACACATGC CCACCGTGCC CAGCACCTGA    60

ATTCGAGGGT GCACCGTCAG TCTTCCTCTT CCCCCCAAAA CCCAAGGACA CCCTCATGAT   120

CTCCCGGACC CCTGAGGTCA CATGCGTGGT GGTGGACGTG AGCCACGAAG ACCCTGAGGT   180

CAAGTTCAAC TGGTACGTGG ACGCCCTCCA GGTCCATAAT GCCAAGACAA AGCCGCGGGA   240

GGAGCAGTAC AACAGCACGT ACCGGGTGGT CAGCGTCCTC ACCGTCCTGC ACCAGGACTG   300

GCTGAATGGC AAGGAGTACA AGTGCAAGGT CTCCAACAAA GCCCTCCCAG CCCCCATCGA   360

GAAAACCATC TCCAAAGCCA AAGGGCAGCC CCGAGAACCA CAGGTGTACA CCCTGCCCCC   420

ATCCCGGGAT GAGCTGACCA AGAACCAGGT CAGCCTGACC TGCCTGGTCA AAGGCTTCTA   480

TCCCAGCGAC ATCGCCGTGG AGTGGGAGAG CAATGGGCAG CCGGAGAACA ACTACAAGAC   540

CACGCCTCCC GTGCTGGACT CCGACGGCTC CTTCTTCCTC TACAGCAAGC TCACCGTGGA   600

CAAGAGCAGG TGGCAGCAGG GGAACGTCTT CTCATGCTCC GTGATGCATG AGGCTCTGCA   660

CAACCACTAC ACGCAGAAGA GCCTCTCCCT GTCTCCGGGT AAATGAGTGC GACGGCCGGC   720

AAGCCCCGCT CCCCGGGCTC TCGCGGTCGC ACGAGGATGC TTCTAGA               767
```

(2) INFORMATION FOR SEQ ID NO:33:

(i) SEQUENCE CHARACTERISTICS:
        (A) LENGTH: 234 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:33:

```
Asp Pro Glu Pro Lys Ser Cys Asp Lys Thr His Thr Cys Pro Pro Cys
 1               5                  10                  15
Pro Ala Pro Glu Phe Glu Gly Ala Pro Ser Val Phe Leu Phe Pro Pro
            20                  25                  30
Lys Pro Lys Asp Thr Leu Met Ile Ser Arg Thr Pro Glu Val Thr Cys
        35                  40                  45
Val Val Val Asp Val Ser His Glu Asp Pro Glu Val Lys Phe Asn Trp
    50                  55                  60
Tyr Val Asp Ala Leu Gln Val His Asn Ala Lys Thr Lys Pro Arg Glu
65                  70                  75                  80
Glu Gln Tyr Asn Ser Thr Tyr Arg Val Val Ser Val Leu Thr Val Leu
                85                  90                  95
His Gln Asp Trp Leu Asn Gly Lys Glu Tyr Lys Cys Lys Val Ser Asn
            100                 105                 110
Lys Ala Leu Pro Ala Pro Ile Glu Lys Thr Ile Ser Lys Ala Lys Gly
        115                 120                 125
Gln Pro Arg Glu Pro Gln Val Tyr Thr Leu Pro Pro Ser Arg Asp Glu
    130                 135                 140
Leu Thr Lys Asn Gln Val Ser Leu Thr Cys Leu Val Lys Gly Phe Tyr
145                 150                 155                 160
Pro Ser Asp Ile Ala Val Glu Trp Glu Ser Asn Gly Gln Pro Glu Asn
                165                 170                 175
Asn Tyr Lys Thr Thr Pro Pro Val Leu Asp Ser Asp Gly Ser Phe Phe
            180                 185                 190
Leu Tyr Ser Lys Leu Thr Val Asp Lys Ser Arg Trp Gln Gln Gly Asn
        195                 200                 205
Val Phe Ser Cys Ser Val Met His Glu Ala Leu His Asn His Tyr Thr
    210                 215                 220
Gln Lys Ser Leu Ser Leu Ser Pro Gly Lys
225                 230
```

(2) INFORMATION FOR SEQ ID NO:34:

(i) SEQUENCE CHARACTERISTICS:
        (A) LENGTH: 19 amino acids
        (B) TYPE: amino acid
        (C) STRANDEDNESS: double
        (D) TOPOLOGY: linear (ix) FEATURE:

(xi) SEQUENCE DESCRIPTION: SEQ ID NO:34:

```
Val Arg Arg Pro Ala Ser Pro Ala Pro Arg Ala Leu Ala Val Ala Arg
 1               5                  10                  15
Gly Cys Phe
```

(2) INFORMATION FOR SEQ ID NO:35:

(i) SEQUENCE CHARACTERISTICS:
        (A) LENGTH: 84 base pairs
        (B) TYPE: nucleic acid
        (C) STRANDEDNESS: double
        (D) TOPOLOGY: linear (ii) MOLECULE TYPE: Other (xi) SEQUENCE DESCRIPTION: SEQ ID NO:35:

```
AACCTGCTCC CATCCTGGGC CATTACCTTA ATCTCAGTAA ATGGAATTTT TGTCATATGC      60

TGCCTGACCT ACTGGTTTGC CCCA                                            84
```

(2) INFORMATION FOR SEQ ID NO:36:

(i) SEQUENCE CHARACTERISTICS:
        (A) LENGTH: 237 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:36:

```
Met Val Ala Gly Ser Asp Ala Gly Arg Ala Leu Gly Val Leu Ser Val
 1               5                  10                  15

Val Cys Leu Leu His Cys Phe Gly Phe Ile Ser Cys Phe Ser Gln Gln
                20                  25                  30

Ile Tyr Gly Val Val Tyr Gly Asn Val Thr Phe His Val Pro Ser Asn
            35                  40                  45

Val Pro Leu Lys Glu Val Leu Trp Lys Lys Gln Lys Asp Lys Val Ala
        50                  55                  60

Glu Leu Glu Asn Ser Glu Phe Thr Ala Phe Ser Ser Phe Lys Asn Arg
 65                 70                  75                  80

Val Tyr Leu Asp Thr Val Ser Gly Ser Leu Thr Ile Tyr Asn Leu Thr
                85                  90                  95

Ser Ser Asp Glu Asp Glu Tyr Glu Met Glu Ser Pro Asn Ile Thr Asp
               100                 105                 110

Thr Met Lys Phe Phe Leu Tyr Val Leu Glu Ser Leu Pro Ser Pro Thr
           115                 120                 125

Leu Thr Cys Ala Leu Thr Asn Gly Ser Ile Glu Val Gln Cys Met Ile
       130                 135                 140

Pro Glu His Tyr Asn Ser His Arg Gly Leu Ile Met Tyr Ser Trp Asp
145                 150                 155                 160

Cys Pro Met Glu Gln Cys Lys Arg Asn Ser Thr Ser Ile Tyr Phe Lys
               165                 170                 175

Met Glu Asn His Leu Pro Gln Lys Ile Gln Cys Thr Leu Ser Asn Pro
           180                 185                 190

Leu Phe Asn Thr Thr Ser Ser Ile Ile Leu Thr Thr Cys Ile Pro Ser
       195                 200                 205

Ser Gly His Ser Arg His Arg Tyr Ala Leu Ile Pro Ile Pro Leu Ala
   210                 215                 220

Val Ile Thr Thr Cys Ile Val Leu Tyr Met Asn Val Leu
225                 230                 235
```

(2) INFORMATION FOR SEQ ID NO:37:

(i) SEQUENCE CHARACTERISTICS:
    (A) LENGTH: 874 base pairs
    (B) TYPE: nucleic acid
    (C) STRANDEDNESS: double
    (D) TOPOLOGY: linear (ii) MOLECULE TYPE: Other (ix) FEATURE:

(xi) SEQUENCE DESCRIPTION: SEQ ID NO:37:

```
GCCCGACGAG CCATGGTTGC TGGCAGCGAC GCGGGGCGGG CCCTGGGGGT CCTCAGCGTG        60
GTCTGCCTGC TGCACTGCTT TGGTTTCATC AGCTGTTTTT CCCAACAAAT ATATGGTGTT       120
GTGTATGGGA ATGTAACTTT CCATGTACCA AGCAATGTGC CTTTAAAAGA GGTCCTATGG       180
AAAAAACAAA AGGATAAAGT TGCAGAACTG GAAAATTCTG AATTCACAGC TTTCTCATCT       240
TTTAAAAATA GGGTTTATTT AGACACTGTG TCAGGTAGCC TCACTATCTA CAACTTAACA       300
TCATCAGATG AAGATGAGTA TGAAATGGAA TCGCCAAATA TTACTGATAC CATGAAGTTC       360
TTTCTTTATG TGCTTGAGTC TCTTCCATCT CCCACACTAA CTTGTGCATT GACTAATGGA       420
AGCATTGAAG TCCAATGCAT GATACCAGAG CATTACAACA GCCATCGAGG ACTTATAATG       480
TACTCATGGG ATTGTCCTAT GGAGCAATGT AAACGTAACT CAACCAGTAT ATATTTTAAG       540
ATGGAAAATC ATCTTCCACA AAAAATACAG TGTACTCTTA GCAATCCATT ATTTAATACA       600
ACATCATCAA TCATTTTGAC AACCTGTATC CCAAGCAGCG GTCATTCAAG ACACAGATAT       660
GCACTTATAC CCATACCATT AGCAGTAATT ACAACATGTA TTGTGCTGTA TATGAATGTT       720
CTTTAATTGA GAAGACAATT TCTTCATTTT TAGGTATTCT GAAATGTGAC AGAAAACCAG       780
ACACAACCAA CTCCAATTGA TTGGTAACAG AAGATGAACA CAACAGCATA ACTAAATTAT       840
TTTAAAAACT AAAAAGCCAT CTGATTTCTC ATTT                                   874
```

(2) INFORMATION FOR SEQ ID NO:38:

(i) SEQUENCE CHARACTERISTICS:
    (A) LENGTH: 824 base pairs
    (B) TYPE: nucleic acid
    (C) STRANDEDNESS: double
    (D) TOPOLOGY: linear (ii) MOLECULE TYPE: Other (ix) FEATURE:

(xi) SEQUENCE DESCRIPTION: SEQ ID NO:38:

```
AAGCTTATGG AGTCAGACAC ACTCCTGCTA TGGGTGCTGC TGCTCTGGGT TCCAGGCTCC        60
ACTGGTGACA TTGTGCTCAC CCAATCTCCA GCTTCTTTGG CTGTGTCTCT AGGGCAGAGA       120
GCCACCATCT CCTGCAGAGC CAGTGAGAGT GTTGAATATT ATGTCACAAG TTTAATGCAG       180
TGGTACCAGC AGAAGCCAGG ACAGCCACCC AAACTCCTCA TCTTTGCTGC ATCCAACGTA       240
GAATCTGGGG TCCCTGCCAG GTTTAGTGGC AGTGGGTCTG GACAAACTT CAGCCTCAAC        300
ATCCATCCTG TGGACGAGGA TGATGTTGCA ATGTATTTCT GTCAGCAAAG TAGGAAGGTT       360
CCTTACACGT TCGGAGGGGG GACCAAGCTG GAAATAAAAC GGGCTTCGGG TGGTGGCGGT       420
TCTGGAGGTG GCGGTTCAGG CGGCGGTGGA TCCCTGGCTC AGGTGCAGCT GAAGGAGTCA       480
GGACCTGGCC TGGTGACGCC CTCACAGAGC CTGTCCATCA CTTGTACTGT CTCTGGGTTT       540
TCATTAAGCG ACTATGGTGT TCATTGGGTT CGCCAGTCTC CAGGACAGGG ACTGGAGTGC       600
CTGGGAGTAA TATGGGCTGG TGGAGGCACG AATTATAATT CGGCTCTCAT GTCCAGAAAG       660
```

```
AGCATCAGCA AAGACAACTC CAAGGGCCAA GTTTTCTTAA AAATGAAGAG TCTGCAAGCT    720

GATGACACAG CCGTGTATTA CTGTGCCAGA GATAAGGGAT ACTCCTATTA CTATTCTATG    780

GACTACTGGG GTCAAGGAAC CTCAGTCACC GTCTCCTCTG ATCA                    824
```

(2) INFORMATION FOR SEQ ID NO:39:

(i) SEQUENCE CHARACTERISTICS:
        (A) LENGTH: 272 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:39:

```
Met Glu Ser Asp Thr Leu Leu Leu Trp Val Leu Leu Trp Val Pro
 1               5                  10                  15

Gly Ser Thr Gly Asp Ile Val Leu Thr Gln Ser Pro Ala Ser Leu Ala
                20                  25                  30

Val Ser Leu Gly Gln Arg Ala Thr Ile Ser Cys Arg Ala Ser Glu Ser
        35                  40                  45

Val Glu Tyr Tyr Val Thr Ser Leu Met Gln Trp Tyr Gln Gln Lys Pro
    50                  55                  60

Gly Gln Pro Pro Lys Leu Leu Ile Phe Ala Ala Ser Asn Val Glu Ser
65                  70                  75                  80

Gly Val Pro Ala Arg Phe Ser Gly Ser Gly Ser Gly Thr Asn Phe Ser
                85                  90                  95

Leu Asn Ile His Pro Val Asp Glu Asp Val Ala Met Tyr Phe Cys
                100                 105                 110

Gln Gln Ser Arg Lys Val Pro Tyr Thr Phe Gly Gly Gly Thr Lys Leu
            115                 120                 125

Glu Ile Lys Arg Ala Ser Gly Gly Gly Gly Ser Gly Gly Gly Gly Ser
    130                 135                 140

Gly Gly Gly Gly Ser Leu Ala Gln Val Gln Leu Lys Glu Ser Gly Pro
145                 150                 155                 160

Gly Leu Val Thr Pro Ser Gln Ser Leu Ser Ile Thr Cys Thr Val Ser
                165                 170                 175

Gly Phe Ser Leu Ser Asp Tyr Gly Val His Trp Val Arg Gln Ser Pro
            180                 185                 190

Gly Gln Gly Leu Glu Cys Leu Gly Val Ile Trp Ala Gly Gly Thr
        195                 200                 205

Asn Tyr Asn Ser Ala Leu Met Ser Arg Lys Ser Ile Ser Lys Asp Asn
    210                 215                 220

Ser Lys Gly Gln Val Phe Leu Lys Met Lys Ser Leu Gln Ala Asp Asp
225                 230                 235                 240

Thr Ala Val Tyr Tyr Cys Ala Arg Asp Lys Gly Tyr Ser Tyr Tyr Tyr
                245                 250                 255

Ser Met Asp Tyr Trp Gly Gln Gly Thr Ser Val Thr Val Ser Ser Asp
            260                 265                 270
```

What is claimed is:

1. A complex comprising a cell and a modified sFv molecule which mediates adhesion between cells, wherein said sFv molecule comprises:
   (a) a variable heavy chain and a variable light chain which recognize and bind a CD28 receptor;
   (b) a Fc region; and
   (c) at least a portion of the transmembrane region of a B7 receptor, wherein said sFv molecule is designated 2e12sFv-hIgG1 (Fc-) fusion protein, and
   wherein said complex is formed between said at least a portion of a transmembrane region of a B7 receptor and the cell membrane of said cell.

2. A complex comprising a cell and a modified sFv molecule which mediates adhesion between cells, said sFv molecule comprising:
   (a) a variable heavy chain and a variable light chain which recognize and bind a first adhesion receptor; and
   (b) at least a portion of a transmembrane region of a second adhesion receptor, wherein at least one of said first adhesion receptor and said second adhesion receptor is B7, and
   wherein said complex is formed between said at least a portion of a transmembrane region of a second adhesion receptor and the cell membrane of said cell.

3. The complex of claim 2, wherein said modified sFv molecule further comprises a Fc region, wherein said Fc region connects said variable heavy and variable light chain to said transmembrane region.

4. A complex comprising a cell and a modified sFv molecule which mediates adhesion between cells, said sFv molecule comprising:
   (a) a variable heavy chain and a variable light chain which recognize and bind a first adhesion receptor;
   (b) a linker region; and
   (c) at least a portion of a transmembrane region of a second adhesion receptor,
   wherein said linker connects said variable heavy and variable light chain to at least a portion of said transmembrane region, and wherein at least one of said first adhesion receptor and said second adhesion receptor is B7, and
   wherein said complex is formed between said at least a portion of a transmembrane region of a second adhesion receptor and the cell membrane of said cell.

5. A complex comprising a cell and a modified sFv molecule which mediates adhesion between cells, said sFv molecule comprising:
   (a) a variable heavy chain and a variable light chain which recognize and bind a CD28 receptor;
   (b) a Fc region; and
   (c) at least a portion of the transmembrane region of a B7 receptor, and
   wherein said complex is formed between said at least a portion of a transmembrane region of a B7 receptor and the cell membrane of said cell.

6. A complex comprising a cell and a modified sFv molecule which mediates adhesion between cells, said sFv molecule comprising:
   (a) a variable heavy chain and a variable light chain which recognize and bind an adhesion receptor; and
   (b) at least a portion of a transmembrane region of a B7 receptor, and
   wherein said complex is formed between said at least a portion of a transmembrane region of a B7 receptor and the cell membrane of said cell.

7. A complex comprising a cell and a modified sFv molecule which mediates adhesion between cells, said sFv molecule comprising:
   (a) a variable heavy chain and a variable light chain which recognize and bind an adhesion receptor;
   (b) a linker region; and
   (c) at least a portion of a transmembrane region of a B7 receptor,
   wherein said linker connects said variable heavy and variable light chain to at least a portion of said transmembrane region of a B7 receptor, and
   wherein said complex is formed between said at least a portion of a transmembrane region of a B7 receptor and the cell membrane of said cell.

* * * * *